(12) United States Patent
Arnold

(10) Patent No.: US 11,515,012 B1
(45) Date of Patent: Nov. 29, 2022

(54) METHOD AND APPARATUS FOR A PIPELINED DNA MEMORY HIERARCHY

(71) Applicant: Mark Gordon Arnold, Bethlehem, PA (US)

(72) Inventor: Mark Gordon Arnold, Bethlehem, PA (US)

( * ) Notice: Subject to any disclaimer, the term of this patent is extended or adjusted under 35 U.S.C. 154(b) by 518 days.

(21) Appl. No.: 16/602,347

(22) Filed: Sep. 19, 2019

Related U.S. Application Data

(60) Provisional application No. 62/765,951, filed on Sep. 22, 2018.

(51) Int. Cl.
| | |
|---|---|
| *G06F 12/06* | (2006.01) |
| *G16B 50/50* | (2019.01) |
| *G16B 50/40* | (2019.01) |
| *G11C 13/02* | (2006.01) |
| *G06N 3/12* | (2006.01) |

(52) U.S. Cl.
CPC ......... *G16B 50/50* (2019.02); *G06F 12/0646* (2013.01); *G06N 3/123* (2013.01); *G11C 13/02* (2013.01); *G16B 50/40* (2019.02); *G06F 2212/251* (2013.01)

(58) Field of Classification Search
CPC ..... G16B 50/50; G16B 50/40; G06F 12/0646; G06F 2212/251; G06N 3/123; G11C 13/02
See application file for complete search history.

(56) References Cited

U.S. PATENT DOCUMENTS

| | | | |
|---|---|---|---|
| 5,705,628 | A | 1/1998 | Hawkins |
| 5,843,661 | A | 12/1998 | Rothemund |
| 2005/0053968 | A1 | 3/2005 | Bharadwaj |

(Continued)

FOREIGN PATENT DOCUMENTS

WO 2017189914 2/2017

OTHER PUBLICATIONS

S. S. Ray, S. Ghosh and R. Prasad, "Low-cost hierarchical memory-based pipelined architecture for DNA sequence matching," 2014 Annual IEEE India Conference (INDICON), 2014, pp. 1-6, doi: 10.1109/INDICON.2014.7030681. (Year: 2014).*

(Continued)

*Primary Examiner* — Ajay Ojha
(74) *Attorney, Agent, or Firm* — Wilkinson Law Office; Clinton H. Wilkinson

(57) ABSTRACT one embodiment of a memory stores information, including address bits, on DNA strands and provides access using a pipeline of tubes, where each tube selectively transfers half of the strands to the next tube based on probing of associated address bits. Transfers are controlled by logic relating to the state of the tubes: The pipeline may be initialized to start at a high-order target address, providing random access without enzymes, synthesizing probe molecules or PCR at access time. Thereafter, a processing unit gets fast access to sequentially addressed strands each cycle, for applications like executing machine language instructions or reading blocks of data from a file. Another embodiment with a compare unit allows low-order random access. Provided that addresses are encoded using single-stranded regions of DNA where probe molecules may hybridize, other information may use any DNA encoding. Electronic/electrochemical (electrowetting, nanopore, etc.) embodiments as well as biochemical embodiments are possible.

26 Claims, 9 Drawing Sheets

Specification includes a Sequence Listing.

(56) References Cited

U.S. PATENT DOCUMENTS

| | | | |
|---|---|---|---|
| 2009/0018809 A1 | 1/2009 | Zimmermann et al. | |
| 2015/0261664 A1 | 9/2015 | Goldman et al. | |
| 2018/0137418 A1 | 5/2018 | Roquet et al. | |
| 2021/0332351 A1* | 10/2021 | Horgan | C12N 15/1068 |

OTHER PUBLICATIONS

Kashiwamura et al., "Hierarchical DNA memory based on nested PCR", Lecture Notes in Computer Science, vol. 2568, pp. 112-123, Jun. 2002.

Milenkovic et al., "Exabytes in a Text Tube: with the Right Coding, DNA Could Archive Our Entire Civilization", IEEE Spectrum, pp. 40-45, May 2018.

Sarkar et al., "Exploring the Feasibility of a DNA Computer: Design of an ALU Using Sticker-Based DNA Model", IEEE Transactions on NanoBioscience, vol. 16, No. 6, pp. 383-399, 2017. DOI: 10.1109/TNB.2017.2726682.

Roweis and Winfree, "A Sticker-Based Model for DNA Computation," Journal Comp. Bio., vol. 5, pp. 615-629, 1996.

Arnold and Martinez-Perez, "Sticker/Staple Algorithms for Forming DNA Origami Nanostructures", poster DNA23, Tempe, Arizona, Sep. 25, 2017.

Arnold and Martinez-Perez, "A Universal Self-Replicating Computer using DNA Sticker CAM", poster DNA25, Seattle, Washington, Aug. 5, 2019.

Arnold, "Improved DNA-sticker Arithmetic: Tube-Encoded-Carry, Logarithmic Number System and Monte-Carlo Methods", Natural Computing, Springer, 2012. doi: 10.1007/s11047-012-9356-3.

Adleman, "Molecular Computation of Solutions to Combinatorial Problems", Science, vol. 266, pp. 1021-1024, 1994.

Takahashi et al., "Demonstration of End-to-End Automation of DNA Data Storage", Scientific Reports, vol. 9, Article No. 4998, 2019.

Willsey et al., "Puddle: A dynamic, error-correcting, full-stack microfluidics platform" Proc. 23rd International Conference on Architectural Support for Programming Languages and Operating Systems, 2019.

Tabatabaei et al., "DNA Punch Cards: Encoding Data on Native DNA Sequences via Topological Modifications", biorxiv.org 10.1101/672394.

Wang et al., "SIMD||DNA: Single Instruction Multiple Data Computation with DNA strand Displacement Cascades", Lecture Notes in Computer Science, vol. 11648, pp. 219-235, Aug. 2019.

Church et al., "Next-Generation Digital Information Storage in DNA", Science, vol. 337, No. 1628, 2012. doi: 10.1126/science.1226355.

Sennels et al., "To DNA, all information is equal", Artif DNA PNA XNA, vol. 3, No. 3, pp. 109-111, 2012. doi: 10.4161/adna.22671.

* cited by examiner

SEQUENCE LISTING

<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: Synthetic oligonucleotide

<400> SEQUENCE: 1
atcggtcata gcact       15

METHOD AND APPARATUS FOR A PIPELINED DNA MEMORY HIERARCHY

CROSS-REFERENCE TO RELATED APPLICATIONS

This application claims the benefit of provisional patent application Ser. No. 62/765,951, filed 2018 Sep. 22 by the present inventor.

SEQUENCE LISTING

The instant application contains a Sequence Listing which has been submitted electronically in ASCII format via EFS-Web and is hereby incorporated by reference in its entirety. Said ASCII copy, created on Dec. 23, 2019, is named 1902AJ522_ST25.txt and is 477 bytes in size.

BACKGROUND—PRIOR ART

U.S. Patents

| Patent Number | Kind Code | Issue Date | Patentee |
| --- | --- | --- | --- |
| 5,705,628 | A | 1994 Jan. 6 | Hawkins |
| 5,843,661 | A | 1998 Dec. 1 | Rothemund |

U.S. Patent Application Publications

| Patent Number | Kind Code | Publ. Date | Applicant |
| --- | --- | --- | --- |
| 20180137418 | A1 | 2018 May 17 | Roquet, et al. |
| 20150261664 | A1 | 2015 Sep. 17 | Goldman et al. |
| 20090018809 | A1 | 2009 Jan. 15 | Zimmermann, et al. |
| 20050053968 | A1 | 2005 Mar. 10 | Bharadwaj |

Foreign Patent Documents

| Number | Cnt | Kind Code | Publ. Date | Applicant |
| --- | --- | --- | --- | --- |
| 2017189914 | WO | A1 | 2017 Feb. 11 | Bathe, et al. |

Nonpatent Literature Documents

S. Kashiwamura et al., "Hierarchical DNA memory based on nested PCR", Lecture Notes in Computer Science, vol. 2568, pp. 112-123, June 2002.

O. Milenkovic et al., "Exabytes in a Text Tube: with the Right Coding, DNA Could Archive Our Entire Civilization", IEEE Spectrum, pp. 40-45, May 2018.

M. Sarkar et al., "Exploring the Feasibility of a DNA Computer: Design of an ALU Using Sticker-Based DNA Model", IEEE Transactions on NanoBioscience, vol. 16, no. 6, pp. 383-399, 2017. DOI: 10.1109/TNB.2017.2726682.

S. Roweis and E. Winfree, "A Sticker-Based Model for DNA Computation," Journal Comp. Bio., vol. 5, pp. 615-629, 1996.

M. G. Arnold and I. M. Martinez-Perez, "Sticker/Staple Algorithms for Forming DNA Origami Nanostructures", poster DNA23, Tempe, Ariz., Sep. 25, 2017.

M. G. Arnold and I. M. Martinez-Perez, "A Universal Self-Replicating Computer using DNA Sticker CAM", poster DNA25, Seattle, Wash., Aug. 5, 2019.

M. G. Arnold, "Improved DNA-sticker Arithmetic: Tube-Encoded-Carry, Logarithmic Number System and Monte-Carlo Methods", Natural Computing, Springer, 2012. doi: 10.1007/s11047-012-9356-3

L. Adleman, "Molecular Computation of Solutions to Combinatorial Problems", Science, vol. 266, pp. 1021-1024, 1994.

C. Takahashi et al., "Demonstration of End-to-End Automation of DNA Data Storage", Scientific Reports, vol. 9, Article no. 4998, 2019.

M. Willsey et al., "Puddle: A dynamic, error-correcting, full-stack microfluidics platform" Proc. 23rd International Conference on Architectural Support for Programming Languages and Operating Systems, 2019.

S Tabatabaei et al., "DNA Punch Cards: Encoding Data on Native DNA Sequences via Topological Modifications", biorxiv.org 10.1101/672394

B. Wang et al., "SIMD∥DNA: Single Instruction Multiple Data Computation with DNA strand Displacement Cascades", Lecture Notes in Computer Science, vol. 11648, pp. 219-235, August 2019.

G. Church et al., "Next-Generation Digital Information Storage in DNA", Science, vol. 337, no. 1628, 2012. doi: 10.1126/science.1226355.

L. Sennels et al., "To DNA, all information is equal", Artif DNA PNA XNA, vol. 3, no. 3, pp. 109-111, 2012. doi: 10.4161/adna.22671

Adleman first suggested that hybridization of artificially designed DNA, together with ligation and enzymes, can store and process digital information. Rothemund (U.S. Pat. No. 5,843,661A) showed such systems are capable of universal (Turing-machine) computation; Zimmerman, et al. suggested a computer gene approach, and Wang et al. (LCNS, 2019) disclose SIMD information processing with DNA. Such techniques are quite cumbersome. Roweiss and Winfree (J. Comp Bio, 1996) suggested a much simpler enzyme-free approach in what they called the sticker system that typically uses magnetic probes, such as beads that attach to DNA as proposed by Hawkins (U.S. Pat. No. 5,705,628). Sakar and Ghosal (Trans. NanoBioscience, 2017) further assumed the sticker system may operate on a single molecule, but such prior-art sticker techniques have not proven cost effective to replace electronic computers. The present inventor has previously proposed techniques (Natural Computing, 2012) that improve computation with stickers, but none of the above prior art has disclosed a method by which DNA may be used to store and execute conventional software (i.e., machine language programs) from a DNA-based memory at the rate of one instruction per cycle.

Separately, there is an increasing need for better archival storage than magnetic media provides. In theory, DNA may offer denser and more long-lasting storage of information than magnetic disk or tape. There are several proposals for systems that function like a DNA disk drive, that is to allow a computer to write an arbitrary file to DNA. For example, Goldman et al. (20150261664A1) report using a base-three encoding (that prevents repeats of A, C, T or G in adjacent positions) to encode files; Bharadwaj (20050053968A1) describes how DNA can encrypt files; Tabatabaei et al. suggest using an enzyme to nick double-stranded DNA leaving a single-stranded region intact as a means of writing bits; and Roquet et al. (20180137418A1) propose ligation of predefined short oligonucleotides on a massive scale to encode large files. Takahashi, et al. (Scientific Reports, 2019) describe completely automated writing and reading of information on DNA using electrowetting hardware known as PurpleDrop, controlled by a high-level language Puddle (Willsey, ASPLOS, 2019). The practicality of DNA as archival storage for electronic computers improves as such automated fluid-handling systems become more cost-effective.

Regardless of how the information is written onto DNA, there is a need for efficient random access, whether to execute machine language branch instructions, or to emulate the seek operation of a disk drive. Typical of the prior art, Takahashi, et al. (Scientific Reports, 2019), S. Kashiwamura et al. (LNCS, 2002) and O. Milenkovic, et al. (IEEE Spectrum, 2018) suggest polymerase chain reaction (PCR) can selectively amplify the strands to be accessed by using primers that hybridize only on those strands. The disadvantages of PCR include: it requires many iterations of thermal cycling; it requires additional slow PCR to continue reading sequentially after the first set of strands; and it contaminates and/or dilutes the supply of strands. Church et al. (Science, 2012) suggests 19-bit address "barcode" (with 1 encoded as A or T) and Bathe et al., (WO2017189914) proposed including sequence address labels on strands. Such address encoding could allow random access but the prior art does not disclose a fast technique to accomplish this. Barcodes or labels in the prior art might allow random access via a probe molecule complementary to the barcode or label, but because the number of strands in a practical system is exponential, such complementary probe molecules would need to be synthesized on the fly for each access, which makes accessing successive addresses slow. Alternatively, all strands could be sequenced simultaneously and reassembled by an electronic computer (as Church et al. did), but such prior-art methods will not scale to the exabyte-size data that the storage density of DNA holds the promise of storing.

SUMMARY

In accordance with one embodiment, a memory hierarchy accesses DNA strands encoding information (including aw address bits probed via hybridization), consists of a processing unit, logic, a memory tube for holding all the strands, and a pipeline of tubes, $T_i$, $1 \leq i \leq aw$, where tube $T_i$ selectively transfers half of its strands to $T_{i+1}$ based on their ith address bit and signals communicated between the tube and the logic. External control bits may specify the initial high-order target address; subsequently a sequence of subsets of strands having desired patterns of address bits are transferred each cycle to the processing unit. An optional compare unit allows the stride of access to be one; many applications may omit the compare unit.

Advantages

Accordingly, the present invention discloses a pipelined DNA memory hierarchy that provides random access to arbitrary addresses (without having to synthesize probe molecules or do PCR at access time), and that provides fast access to sequential addresses thereafter. Such properties make the present invention desirable in many application contexts, including the sequential execution of machine language instructions and the sequential reading of successive blocks of data from a disk file. The present invention is related to the simple sticker system in that it avoids enzymes, ligation, PCR, etc. but the present invention does not necessarily require that information be encoded using stickers. Most of the prior art methods of writing data onto DNA are compatible with the present invention. The key requirement is the address be encoded using a plurality of single-stranded regions of DNA that allow probe molecules to test individual bits of the address. Because a small set of probe molecules allow access to an exponentially large address space, the probe molecules do not have to be synthesized on the fly.

DRAWING—FIGURES

FIG. 1 shows a block diagram of a 5-bit memory hierarchy including a memory tube and five pipeline tubes (either labeled as bold-upper-case $T_5$-$T_1$ for big-endian-one-origin notation or bold-lower-case $t_0$-$t_4$ for little-endian-zero-origin notation), together with logic and control. The logic and thin arrows (signals $s_i$, $c_i$, $f_i$, etc.) connecting to the logic may implemented either electronically or biochemically; the tubes and thick arrows (pipes) are implemented at least in part biochemically. An optional compare unit may be omitted if random access is only limited to addresses whose low-order bits are zero.

Figure 4:
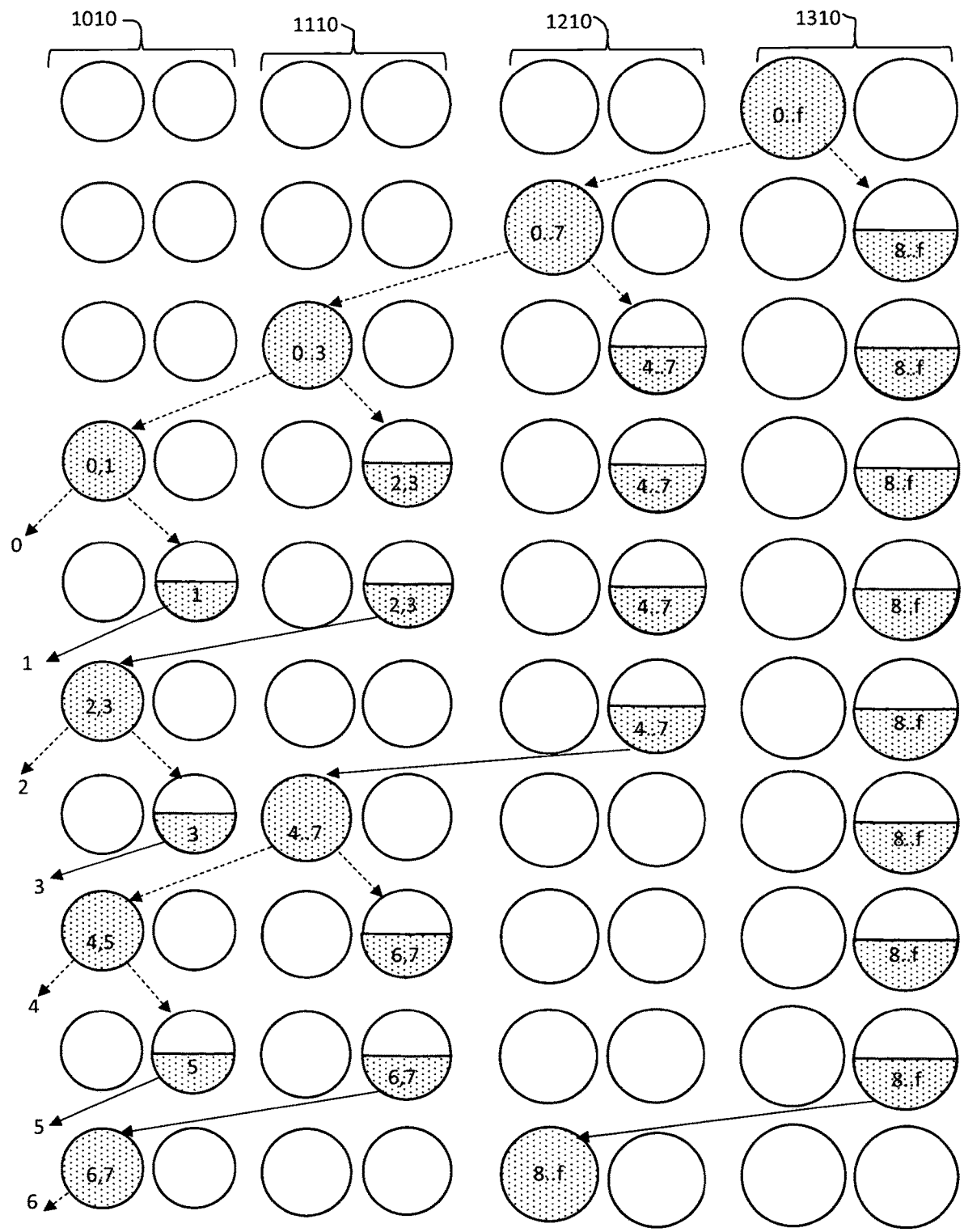

FIG. 4. illustrates an alternative implementation using two subtubes ($s_i$ and $c_i$) per tube where the $s_i$ and $c_i$ can be determined by which subtube is not empty.

Figure 5:
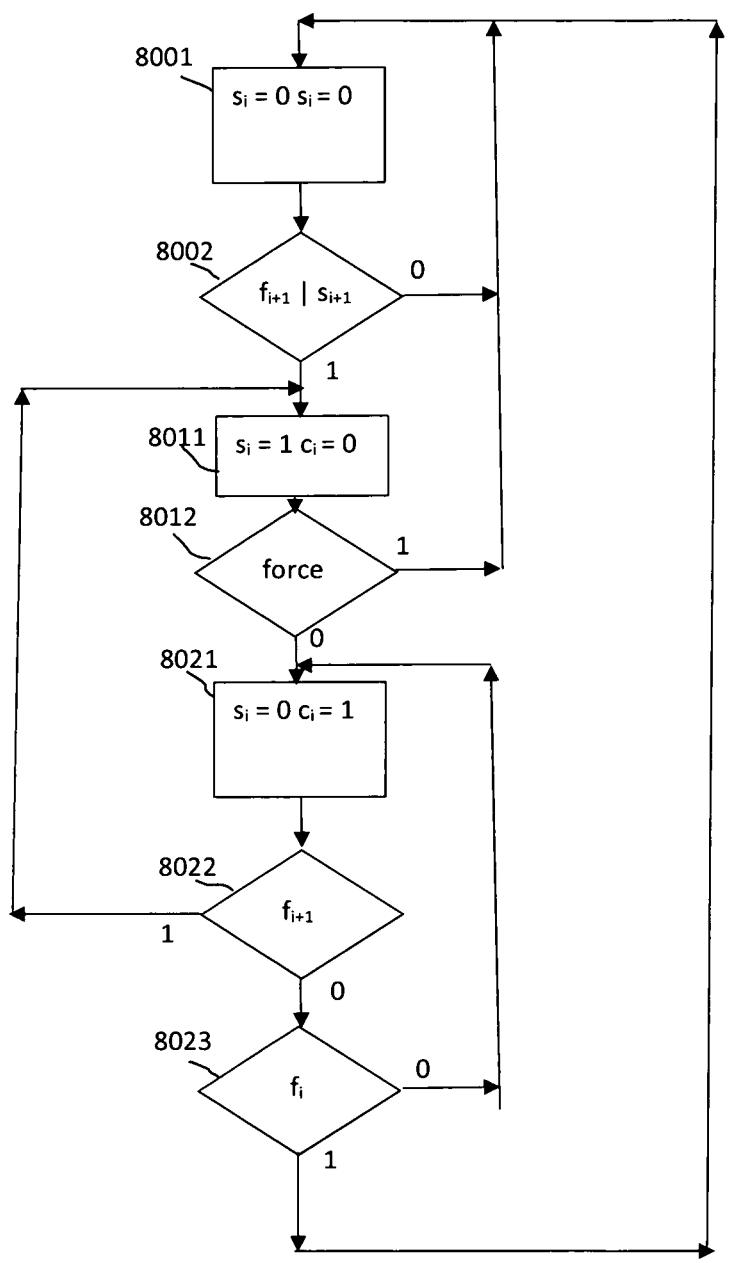

FIG. 5 shows how the $s_i$ and $c_i$ status may be generated by an Algorithmic State Machine, rather than by measuring the number of strands in the tube.

Figure 6:
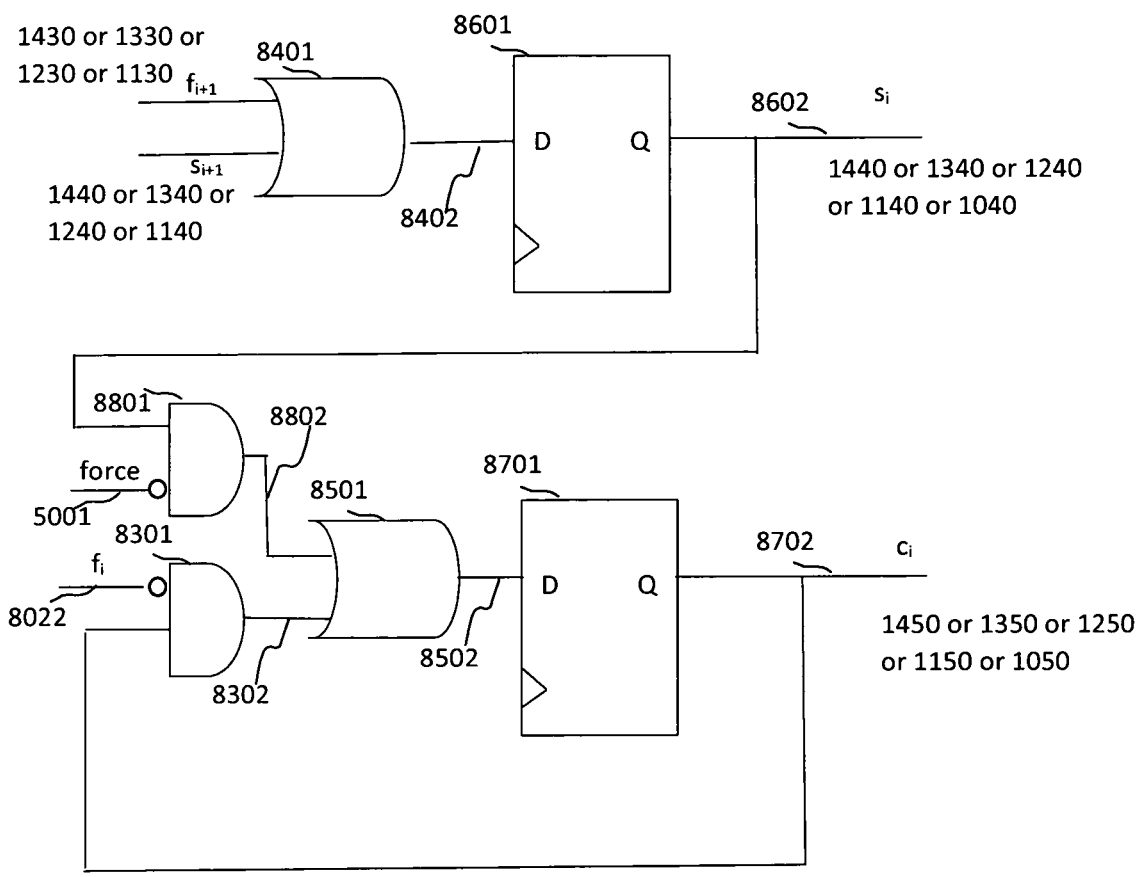

FIG. 6 gives an electronic state machine equivalent to FIG. 5.

Figure 7:
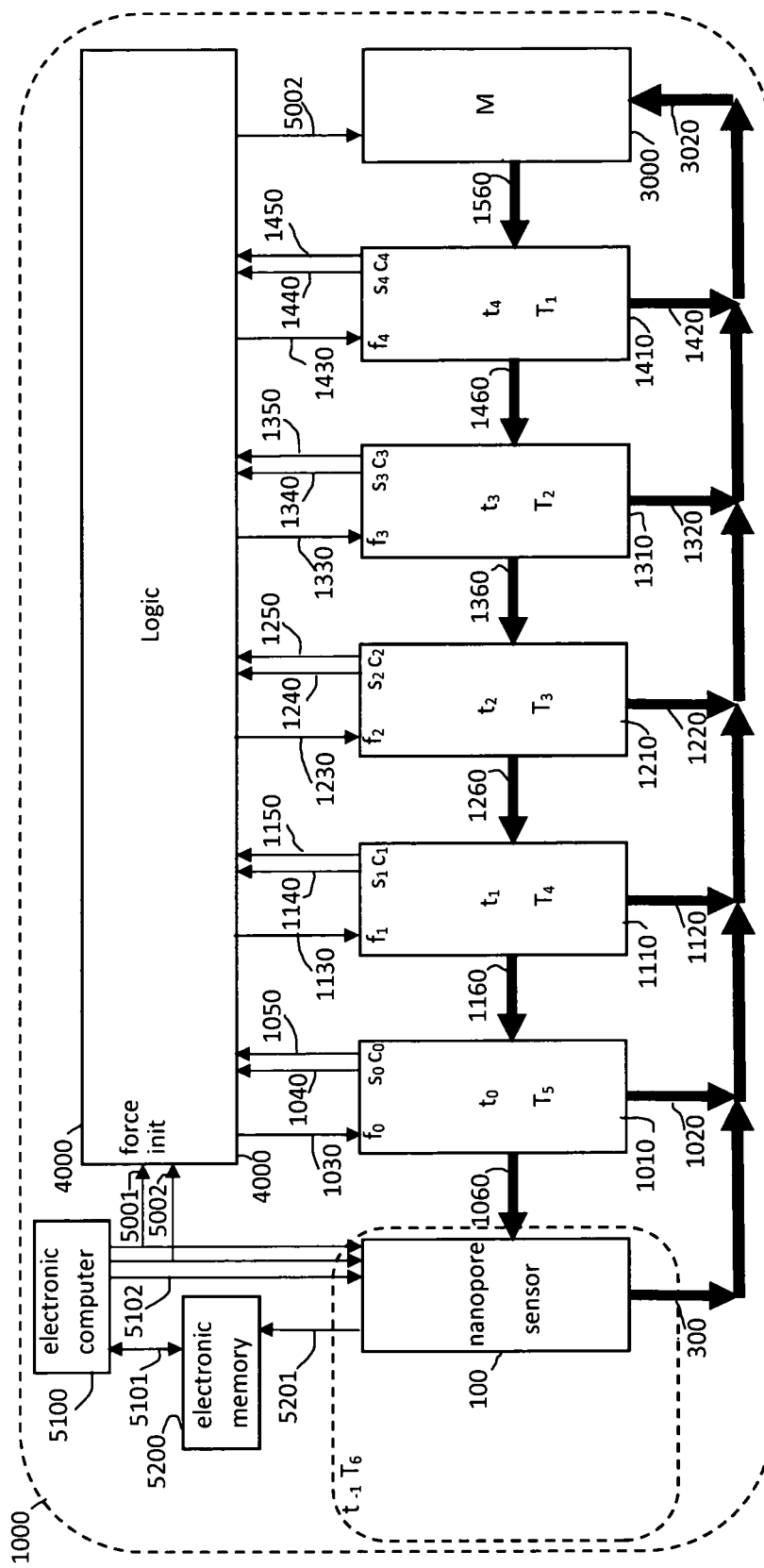

FIG. 7 shows an example application using the present invention to implement a DNA disk drive attached to an electronic computer and electronic memory.

Figure 8:
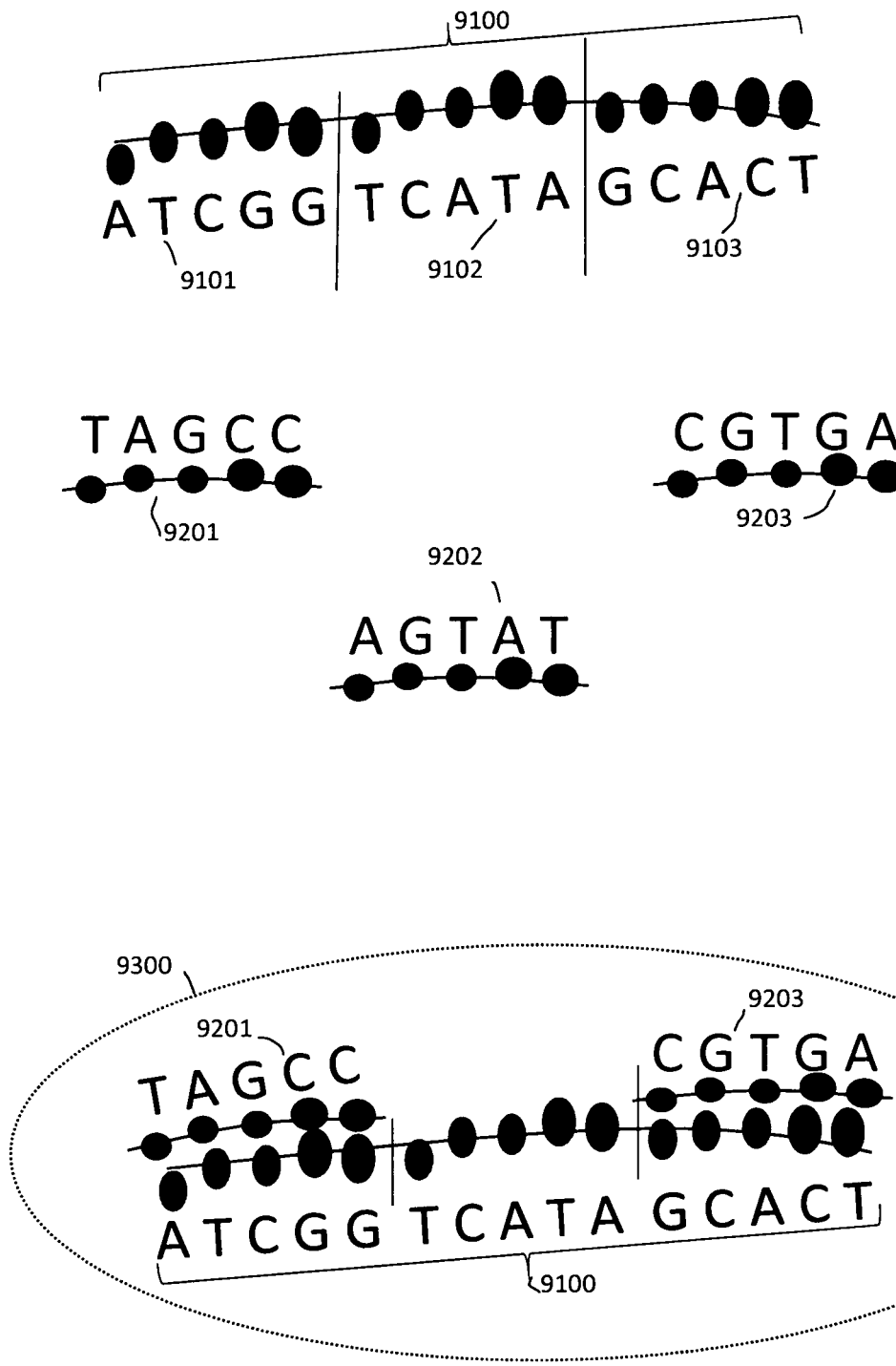

FIG. 8 illustrates one possible prior-art biochemical computing context in which the present invention could be implemented, the Roweis-Winfree Sticker System.

Figure 9:
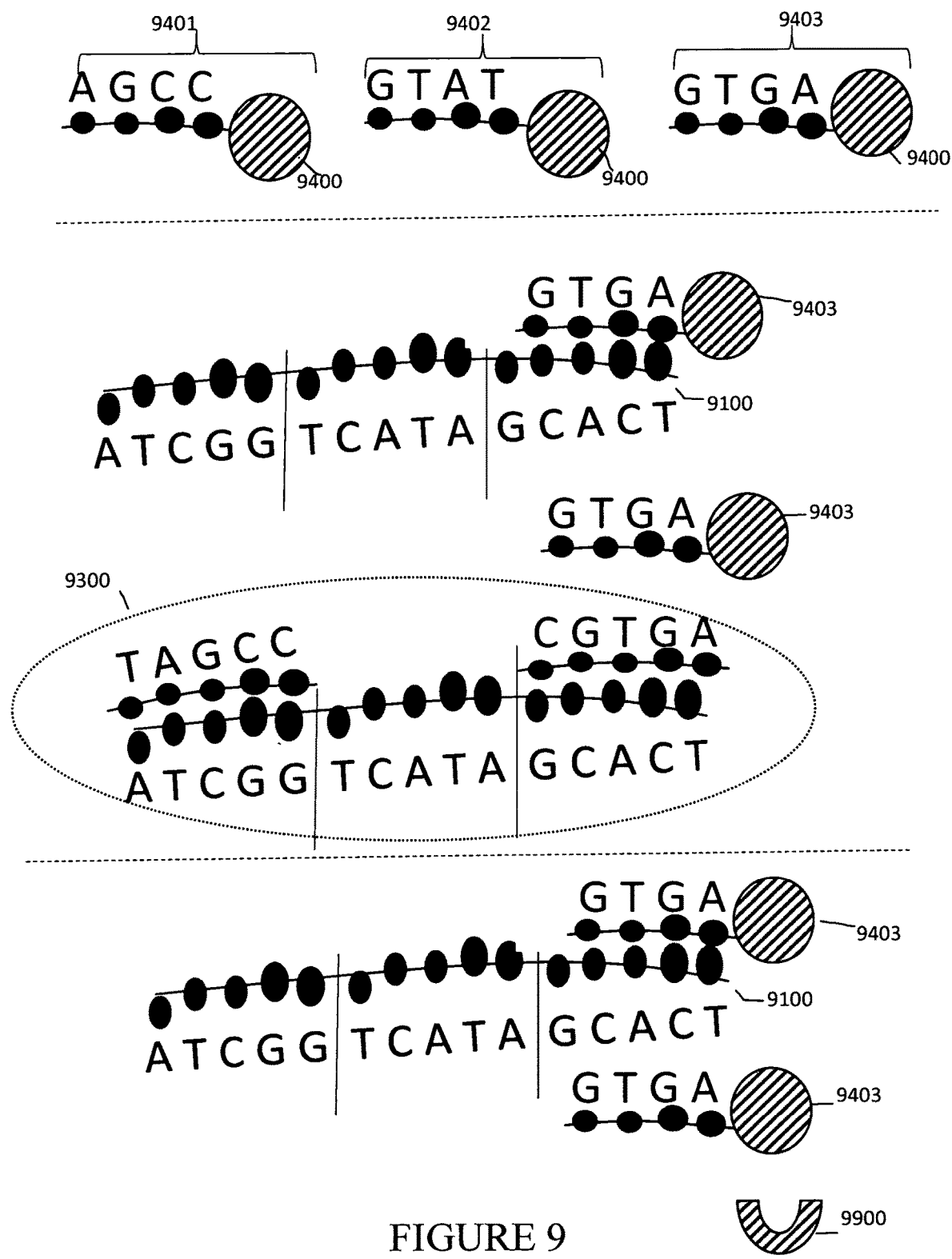

FIG. 9 illustrates the use of magnetic bead probes as a possible implementation of the probing by hybridization used in the present invention.

DETAILED DESCRIPTION

Figure 1:
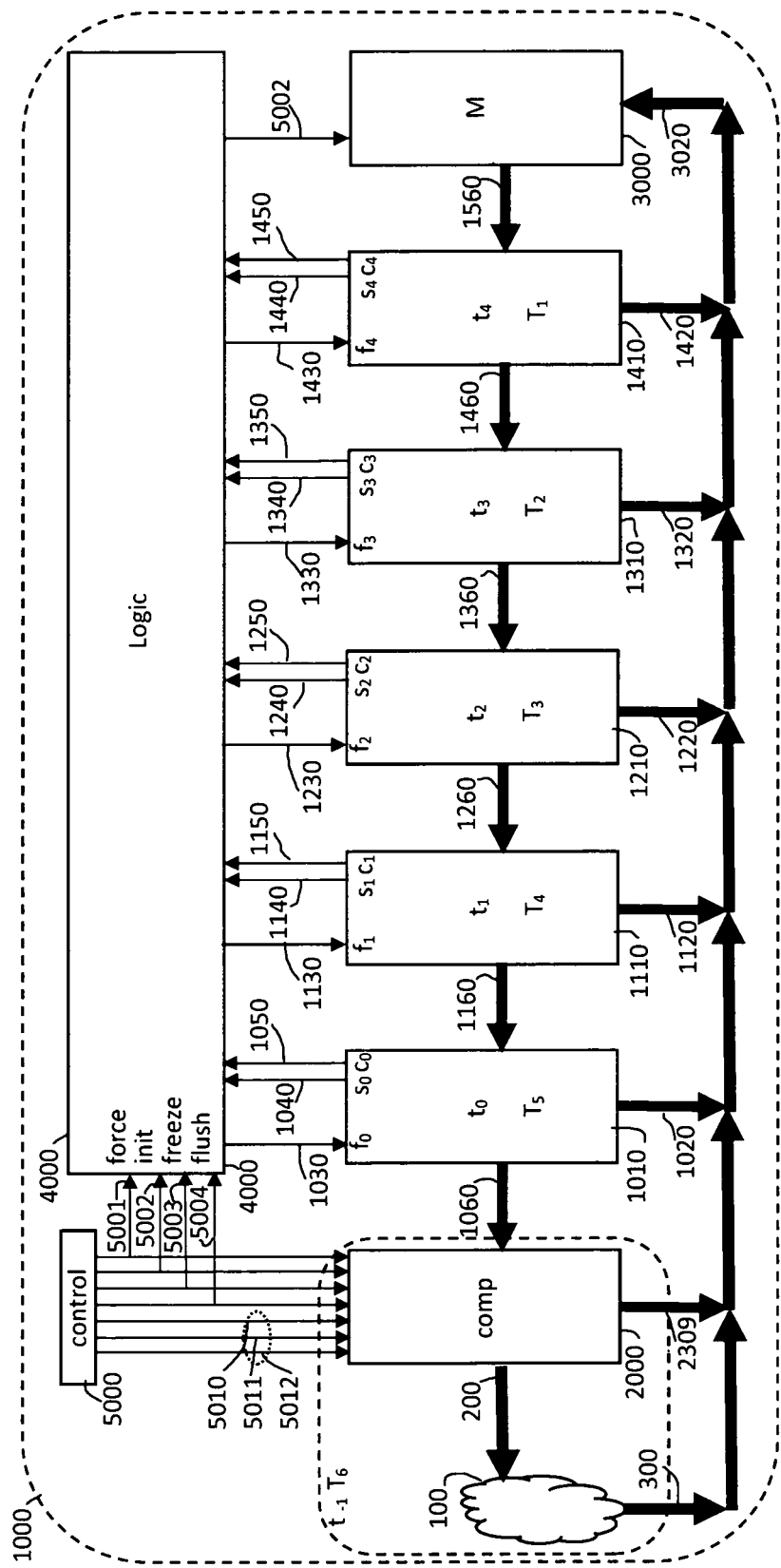

Referring to FIG. 1, an example pipelined DNA memory hierarchy 1000 works with DNA memory strands whose address width (aw) is 5; an arbitrary number of additional bits are treated as corresponding data. Those skilled in the art will understand how to implement a similar DNA memory hierarchy for other values of aw. Those skilled in the art will also realize that the present invention allows memory hierarchies with other biochemical molecules, such as RNA, PNA, XNA, etc. The key requirement is that the value of a bit is encoded somehow in a single-stranded region of the molecule that may be probed via a biochemical hybridization. Those skilled in the art will also recognize each bit may be represented either a) in Adleman way of using unique patterns of A,C,T and G bases (such patterns are sometimes called DNA codewords) for both '0' and '1' at each bit position (number of unique codeword patterns is twice the number of bit positions but only half of those are used on any particular strand); or b) in the Roweiss-Winfree way of using unique patterns of A,C,T and G at each bit position and using short complementary stickers to distinguish between '0' and '1' (number of unique codeword patterns on every strand is the same as the number of bit positions but up to that number of complementary stickers may be placed differently on each strand). Those skilled in the art will understand that the DNA codewords are chosen so that they do not interact with each other. The present invention assumes such information has already been written onto the DNA strands. In the Adelman way of encoding information, the data can be written to the DNA strands by synthesizing artificial oligonucleotides using standard biochemical techniques such as ligation, or from snippets of naturally occurring DNA. As taught in Roquet et al., this Adleman way of encoding information may ligate distinct codewords for both '1' and '0' (as described above), or only ligate codewords for either the '1's or the '0's. Bits may be encoded on naturally occurring double-stranded DNA by nicking regions (Tabatabaei et al., 2019) identified to act as codewords so that the single-stranded region is exposed (and able to be probed). Examples here assume each codeword uses the same number of bases, and codewords are contiguous to each other on the strand, but those skilled in the art could implement the present invention using non-contiguous and/or unequal-size codewords. The ability to probe is only relevant for the address bits used by the present invention; the other information carried on the strand may be coded in the same or different way(s).

Referring to FIG. 8 which is an example to illustrate one possible prior-art biochemical environment (the Roweis-Winfree sticker system) in which the present invention may operate, numerous copies of several species of single-stranded DNA are available in separate tubes. One of these species, simply known as a strand 9100 (SEQ ID NO: 1), has several codeword regions 9101, 9102, 9103. This three-bit (three codeword) example illustrates the first codeword 9101 using a pattern of five bases (ATCGG). The example chooses TCATA for second codeword 9102 and GCACT for third codeword 9103. A collection of these identical to strand 9100 are kept in a tube. Another tube contains a short complementary segment known as sticker 9201. The pattern of sticker 9201 (TAGCC) is complementary to codeword region 9101 of sticker 9100. Similarly, two additional tubes contain sticker 9202 (AGTAT) and sticker 9203 (CGTGA), which have complementary patterns to the associated codeword regions 9102 and 9103 of sticker 9100. Writing bits that are '1' in the sticker system occurs by combining the stickers associated with those bits into the tube that contains the strand 9100 and allowing hybridization to occur. For example, the three-bit value '101' is encoded as the complex 9300 consisting of strand 9100 hybridized to stickers 9201 and 9203. Again, those skilled in the art will recognize the present invention is compatible with, but does not require, this prior-art sticker method of writing bits.

Referring to FIGS. 8 and 9, the three-bit example continues with magnetic probe molecules 9401, 9402 and 9403, which are similar to stickers 9201, 9202 and 9203 except probe molecules have a magnetic bead 9400 attached. It is probably advantageous for the complementary sequence to be shorter than that of a sticker so that the melting point of the probe is below that of any sticker, allowing probes 9401, 9402 and/or 9403 to be detached from a strand by heating the contents of a tube to a predetermined temperature without disturbing stickers 9201, 9202 or 9203. Those skilled in the art will realize other hybridization probe techniques are possible to use with the present invention, such as probe molecules attached to the walls of special tubes (as simulated by Verilog code given later).

Suppose a tube ($T_0$) that contains naked strand 9100 (representing '000') and strand complex 9300 (representing '101') has a series of identical molecules like probe 9403. One will hybridize with the naked strand 9100 because the associated bit position is a '0'. Another will remain unhybridized, leaving strand complex 9300 free to move about in the solution that contains the strands.

If an external magnetic field 9900 is applied, and the solution is forced out of the tube, the complex 9300 will be carried away (presumably to another tube, $T_1$, not shown), leaving the naked strand 9100 attached to the magnetic probe 9303. The magnetic probe 9303 may be melted away and magnetically removed, leaving the strand with a bit '0' separated from a strand with a bit of '1'. The sticker system conceptualizes this as an algorithmic step, SEPARATE($T_1$, $T_0$, $T_0$, bitpos).

Referring to FIG. 1, the pipelined DNA memory hierarchy 1000 generally transfers one DNA memory strand via pipe 200 to an arbitrary processing unit 100 each clock cycle. This description assumes a synchronous implementation where a clock signal is provided by some electrical or chemical means, but those skilled in the art will recognize similar pipelines may be implemented by asynchronous means.

Simultaneously, the processing unit 100 may return a previous memory strand to the pipelined DNA memory hierarchy 1000 via pipe 300 because under normal circumstances neither the processing unit 100 nor the pipelined DNA memory hierarchy 1000 creates or destroys DNA strands. A typical application of pipelined DNA memory hierarchy 1000 is where processing unit 100 treats the data portion of DNA memory strands as conventional machine language instructions to be executed. Those skilled in the art will understand the datapath of such an execution unit would also be pipelined, and processing unit 100 might take several pipeline stages before it returns a particular DNA memory strand via pipe 300. An entirely different application of pipelined DNA memory hierarchy 1000 would be the assembly of larger DNA nanostructures from individual mostly single-stranded DNA delivered to processing unit 100 from pipelined DNA memory hierarchy 1000 in the order they need to be attached to the nanostructure (Arnold, et al. 2017). In such applications, the processing unit 100 consumes the DNA strands, and they would not be returned via pipe 300. One can imagine other applications where circular mostly double-stranded plasmid-like DNA strands (only the address portion is uncovered) are used by processing unit 100 for protein synthesis before being returned via pipe 300. Yet another application is as a DNA Disk drive attached to a conventional electronic computer.

Regardless of the application envisioned for processing unit 100, during normal operation, one memory strand will appear each clock cycle in the sequential order defined by the address portion of the DNA strands. For example, with five-bit binary address DNA memory strands (consistent with the example aw=5 of FIG. 1), if the binary address 00010 were to appear on the DNA memory strand transferred via pipe 200 during the current clock cycle, normally that strand would be returned via pipe 300 during the next cycle while simultaneously the binary address 00011 would appear on the DNA memory strand transferred via pipe 200, and so forth (00100, 00101, etc.).

The pipelined DNA memory hierarchy 1000 includes a controller 5000 interconnected with logic 4000. The signals sent from controller 5000 to logic 4000 include the force signal 5001, the initialize signal 5002, the freeze signal 5003 and the flush signal 5004; these signals 5001, 5002, 5003 and 5004 deal with abnormal or atypical conditions. The controller 5000 and logic 4000 may be implemented electronically using digital logic and/or microprocessors. Alternatively, the controller 5000 and logic 4000 may be implemented biochemically. The controller 5000 and logic 4000 sequence the remaining components of the DNA memory hierarchy 1000, which may be implemented electrochemically (e.g., electrowetting as in PurpleDrop) or biochemically (machinery built from other kinds of DNA, RNA, protein, etc. molecules that act to contain and process the distinct Adleman-like or Roweiss-like DNA strands that records the address and data being discussed from this point on).

These electrochemical-or-biochemical components include an optional comparison unit 2000 (which assists in initial random accessing of an arbitrary binary starting address so that the first DNA strand output via pipe 200 matches the desired low-order starting address, i.e., earlier addresses are filtered out) and a series of DNA tubes 1010, 1110, 1210, 1310, 1410, . . . , 3000. The comparison unit is unnecessary if low-order ceil($\log_2$(aw)) bits of the starting address are zero, and in certain special cases, but is necessary for arbitrary (stride one) random access. DNA tube 3000 at times may hold all the DNA memory strands prior to initial random access. This memory tube 3000 is sometimes called M. The other tubes 1010, 1110, 1210, 1310, 1410, . . . may hold various subsets of the DNA memory strands in a pipelined process that arranges them into sequential order for eventual output from comparison unit 2000 via pipe 200. In little-endian-zero-origin notation tube 1010 is called to, where the lower-case-bold indicates the choice of this notation, which is used in source code descriptions later. Those skilled in the art will realize an identical apparatus can be described in other ways, such as big-endian-one-origin notation, where tube 1010 is called $T_{aw}$, which in this example would be $T_5$. Tubes 1110, 1210, 1310, 1410 may be referred to as $t_1$, $t_2$, $t_3$ and $t_4$ or as $T_4$, $T_3$, $T_2$ and $T_1$. Using big-endian-one-origin notation may be considered easier to describe these tubes in English, but those skilled in the art will realize, although the descriptions in the two notations are different because the subscripts are transformed, they describe identical ideas.

Successively smaller subsets of DNA strands are transferred via pipes 1560, . . . , 1460, 1360, 1260, 1160 and 1060. Pipe 1060 transfers at most one strand (there may be redundant copies of this one strand) per cycle to be filtered (if necessary) by comparison unit 2000 before being output on pipe 200. The signals sent from controller 5000 to comparison unit 2000 include the desired-starting-address low-order bits 5010, 5011, 5012, . . . , the force signal 5001, the initialize signal 5002, the freeze signal 5003 and the flush signal 5004. The initialize signal 5002 changes the internal state of comparison unit 2000 so that it discards (via pipe 2309) strands input via pipe 1060 until it finds a strands whose low-order address bits match desired-starting-address low-order bits 5010, 5011, 5012, . . . Finding such a strand alters the state of the comparison unit 2000 so that for normal operation from that moment onward it passes through (to pipe 200) all strands input via pipe 1060. This is the reason why controller 5000 occasionally needs to assert the initialize signal 5002 when it wants to alter the normal operation of the pipeline. The initialize signal 5002 also causes memory tube 3000 to transfer its contents via pipe 1560 to the adjacent tube, which in the five-bit example of FIG. 1. is tube 1410, and this begins the pipelined process.

The logic 4000 generates 3-bit tube controls 1030, 1130, 1230, 1330, 1430, . . . corresponding to the respective DNA tubes 1010, 1110, 1210, 1310, 1410, . . . Each of the 3-bit controls 1030, 1130, 1230, 1330, 1430, . . . allows for eight distinct behaviors of the corresponding tubes 1010, 1110, 1210, 1310, 1410, . . . during a clock cycle. Those skilled in the art will realize other arrangements besides 3-bit controls are possible. During normal operation, (when strands appear in pipe 200 in sequential order), each control signal will indicate that the corresponding tube should perform either a) combining strands currently residing in the tube with strands transferred from the tube's right input (no strands are transferred out of the tube during such a cycle); b) transferring strands currently in the tube towards the unit on the left while simultaneously and independently transferring strands from the tube's right input to become the new tube contents (the biochemical equivalent of a flip flop); or c) separating and transferring strands currently in the tube that record a '0' in a particular bit position to the unit on the left while simultaneously and independently combining strands that record a '1' in that bit position with any strands transferred from the tube's right input. Those skilled in the art of digital design will realize that the role of '0' and '1' may be interchanged. The bit-position within the strand that is tested is a design parameter that is distinct in each of the tubes 1010, 1110, 1210, 1310, 1410, . . . At times other than normal operation (such as initial random access, flushing or freezing the pipeline) a tube needs additional commands, such as sending strands to be recycled into the memory tube 3000, which will be discussed in more detail later.

Each of the DNA tubes 1010, 1110, 1210, 1310, 1410, . . . is designed to recognize whether it holds approximately more or less than a particular number of strands. This number is some constant (including r, the number of strands that are redundant with identical information on each strand, or that at least have identical address bits if distinct information is recorded in the non-address portion of the strand) times two raised to the bit-position parameter described in the separate operation. This predetermined midpoint (n') parameter of DNA tube 1110 is twice this parameter of DNA tube 1010, and so forth proceeding from left to right in FIG. 1 because DNA tube 1110 separates based on bit position 1, whereas DNA tube 1010 separates based on bit position 0, etc. The midpoint might be more conveniently defined as $3n'/4=1.5r2^{i-1}$ to allow for some tolerance in the approximate comparison since the tube contains either $2^i$ or $2^{i-1}$ strands. Again, the numbering of bit positions is subject to the notational distinction of little-endian-zero-origin (which is what the preceding sentences used) versus big-endian-one-origin.

Each of the DNA tubes 1010, 1110, 1210, 1310, 1410, . . . generates an $s_i$ status signal 1040, 1140, 1240, 1340, 1440, . . . when the particular DNA tube holds more strands than its corresponding design parameter; each of the DNA tubes 1010, 1110, 1210, 1310, 1410, . . . generates an $c_i$ status signal 1050, 1150, 1250, 1350, 1450, . . . when the particular DNA tube is not empty but holds fewer strands than its corresponding design parameter. The $s_i$ and $c_i$ are not bold because they are not tubes. They are simple signals that may be implemented biochemically, electrically, or electrochemically. Their subscripts correspond to the subscripts of the tubes and should be consistent. Here, lower case indicates little-endian-zero-origin. Analogous big-endian-one-origin description for these signals would be $C_i$ and $S_i$.

Figure 3:
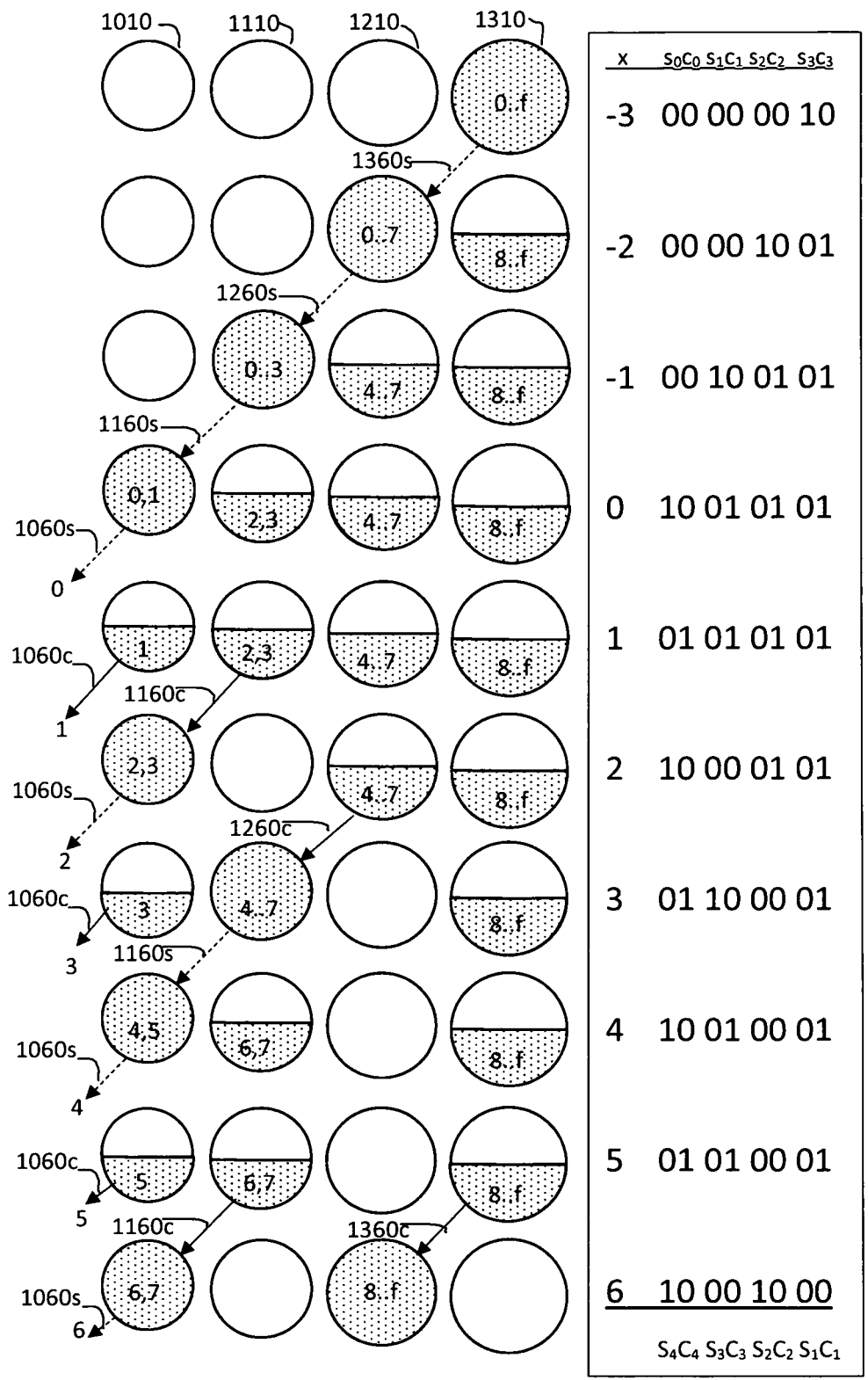
FIG. 3 illustrates how the tubes in FIG. 1 operate over the first ten pipeline cycles given an initial set of sixteen strands whose addresses are shown by hexadecimal digits 0 through f. There is a corresponding chart that shows how the $s_i$ and $c_i$ status signals from FIG. 1 can be determined from how full the tubes are.

Referring to FIG. 3, the tubes 1310, 1210, 1110 and 1010 from FIG. 1 are shown in the first ten pipeline cycles, given an initial set of sixteen strands whose addresses are show by hexadecimal digits 0 through f. The diameter of tubes 1310, 1210, 1110 and 1010 is meant to suggest (symbolically, not proportionately) that tube 1310 holds more strands than tube 1210, which holds more strands than tube 1110, etc. FIG. 3 also has a corresponding chart that shows pipeline cycle number x, and how the $s_i$ and $c_i$ (also labeled with big-endian $S_i$ and $C_i$) status signals at time x can be determined from how full the tubes are. As a notational convention, the value of x is negative during pipeline initialization. At the start (x=−3), tube 1310 is completely full (strands 0 . . . f); the other tubes 1210, 1110 and 1010 are empty. The $s_i$ and $c_i$ values in the table "00 00 00 10" reflect this measurement. In the next pipeline initialization cycle (x=−2), tube 1310 has separated half its contents (0 . . . 7) to tube 1210 via pipe 1360*s*. The pipe 1360*s* is shown as a dotted line here (and has a reference number with "s" suffix) because a "separate" operation has occurred, and the other half of the strands (8 . . . f) remain in tube 1310. The $s_i$ and $c_i$ values in the table "00 00 10 01" reflect the fact tube 1210 is full (its capacity is half that of tube 1310), but tube 1310 is now half full. A similar situation occurs at x=−1, where tube 1210 has separated half its contents (0 . . . 3) to tube 1110 via pipe 1260*s*, leaving the other half (4 . . . 7) in tube 1210. The $s_i$ and $c_i$ values in the table "00 10 01 01" now indicate tube 1110 is full, while tubes 1210 and 1310 remain half full. At x=0, tube 1010 has separated half its contents (0,1) to tube 1010 via pipe 1160*s*, leaving the other half (2,3) in tube 1110. The $s_i$ and $c_i$ values in the table "10 01 01 01" now indicate tube 1010 is full, while tubes 1110, 1210 and 1310 remain half full. Finally after cycle x=0 is complete, the pipeline begins to output the first strand (0) via pipe 1060*s*, which is again shown as a dotted line because it is a separate operation, leaving only (1) in tube 1010, which is indicated by "01 01 01 01".

After initialization is complete, at time x=1, things get more involved. Simultaneously, tube 1010 transfers the remaining stand (1) via pipe 1060*c* as output, while tube 1110 transfers its contents (2,3) to tube 1010 via pipe 1160*c*. Between x=1 and x=2, pipes 1060*c* and 1160*c* are shown as solid lines and have the "c" suffix because these are total transfers (in sticker terminology, "COMBINE" operations). The net effect at time x=2 makes tube 1010 full with new contents (2,3), but leaves tube 1110 empty, a situation shown as "10 00 01 01". Between x=2 and x=3, pipe 1260*c* transfers the entire contents of tube 1210 to tube 1110 and pipe 1060*s* separates out the next output (2), leaving 3 in tube 1010. Also, simultaneously, tube 1210 transfers (via solid line 1260*c*) its remaining contents (4 . . . 7) into tube 1110. At x=3, this new situation is shown as "01 10 00 01". Between x=3 and x=4, pipe 1060*c* outputs 3. Also, tube 1110 separates half its strands (4,5) via pipe 1160*s* to tube 1010, leaving the other half (6,7) in tube 1110. At x=4, this is shown as "10 01 00 01". Between x=4 and x=5, there are no transfers between tubes. Since 4 has been output from tube 1010, it is half full with the other tubes unchanged, and this appears as "01 01 00 01". Between x=5 and x=6, the entire contents (6,7) of tube 1110 is transferred to tube 1010 via pipe 1160*c*, and the entire contents (8 . . . f) of tube 1310 is transferred to tube 1210 via pipe 1360*c*, which is shown as "10 00 10 00".

If it is difficult to implement a tube that distinguishes such numbers of strands, an equivalent tube may be implemented by using two subtubes: an $s_i$ subtube that holds the full number and its non-empty condition indicates more than the particular number of strands and a $c_i$ subtube that holds half that number as a result of the separating operation that emptied the $s_i$ subtube; testing the emptiness of these two subtubes gives the information needed in the previous paragraphs. Like tubes, subtubes are shown in bold. Again, the lower case indicates little-endian-zero-origin. Analogous big-endian-one-origin description is possible with upper-case-bold $C_i$ and $S_i$. Referring to FIG. 4, the same example as FIG. 3. is shown where tubes 1310, 1210, 1110 and 1010 are implemented as subtubes. Note the same information as shown in the table in FIG. 3 can be observed directly from the emptiness of the subtubes.

If both the subtube approach and the approach of measuring the approximate number of strands against the midpoint parameter prove too costly to implement, the $s_i$ and $c_i$ status may be generated by digital electronic logic. Referring to FIG. 5, an alternative implementation that avoids the need to measure whether tubes are empty is shown using a digital electronic controller, specified by an Algorithmic State Machine (ASM) chart, consisting of three states. There will be one such ASM per tube, $t_i$, which is why the ASM uses i subscripts. Each of these ASMs operate concurrently to the pipeline. This figure assumes little-endian-zero-origin notation, meaning more significant bits are referred to with larger subscripts. Those skilled in the art will understand to substitute $F_{i-1}$ for $f_{i+1}$, etc. if big-endian notation were preferred. The state machine begins in state 8001. State 8001 includes a decision 8002 which tests the $f_{i+1}$ and $s_{i+1}$ inputs. The purpose of state 8001 and associated decision 8002 is for leaving $s_i$ and $c_i$ in their unasserted (0) condition until the $f_{i+1}$ or $s_{i+1}$ controlling the next more significant tube ($t_{i+1}$) indicates that tube is scheduled to transfer new strands into the tube in question ($t_i$). Rather than measuring the physical presence of these strands in the next cycle, the ASM predicts them by making a state transition to state 8011. The purpose of state 8011 is for asserting the $s_i$ status for one cycle. When force is not asserted, half of the strands are destined to stay the tube in question after one cycle. State 8011 has a decision that causes transition back to state 8001 when force is asserted, but normally makes a transition to state 8021 in the more typical case when force is not asserted. State 8021 includes a decision 8022 which tests the $f_{i+1}$ input from the logic 4000 while $c_i$ is also being asserted. This situation is only relevant for i=0. If $f_{i+1}$ is asserted in state 8021, the ASM transitions to state 8011, which allows for the scscsc . . . pattern that only happens for i=0. Otherwise, state 8021 also includes a decision 8023 which tests the $f_i$ input from the logic 4000 that controls the tube in question. The primary purpose of state 8021 and associated decision 8023 is for asserting the $c_i$ status until the $f_i$ command indicates the tube in question will empty into the less significant tube ($t_{-1}$). The ASM will stay in state 8021 until the $f_i$ command is asserted, at which time the ASM repeats back to state 8001. Referring to FIG. 6, a possible digital electronic hardware implementation of the ASM chart, uses a D-type flip flop 8601 for storing $s_i$ and another D-type flip flop 8701 for storing $c_i$. These are clocked at the same rate as the pipeline. The flip flop 8601 is loaded with the output 8402 of OR gate 8401, which ORs $f_{i+1}$ command (1430, 1330, 1230 or 1130) and $s_{i+1}$ status (1440, 1340, 1240 or 1140) from the previous pipeline cycle. In the case of i=aw, the $s_{i+1}$ status and $f_{i+1}$ command are defined to be the initialize signal 5002. This flip flop 8601 outputs on wire 8602, which connects to the appropriate signal such as 1440, 1340, 1240, 1140 or 1040. There is an OR 8501 whose output 8502 is the input to flip flop 8701. The inputs to OR 8501 are wires 8302 and 8802. Wire 8802 is the output of AND gate 8801, whose inputs are $s_i$ status 8602 and the complement of force signal 5001. In the typical case when force signal 5001 is not asserted, the $s_i$ input 8602 causes the $c_i$ output 8702 of flip flop 8701 to be asserted in the cycle after $s_i$ output was asserted. The other input 8302 of OR 8501 is the output of AND 8301, whose inputs are a complemented $f_i$ command 8022 and the $c_i$ output 8702 of flip flop 8701. This has the effect of keeping the $c_i$ status asserted when it was asserted in the previous cycle and the $f_i$ command was unasserted.

There are two ways to indicate the state of the pipeline. The most natural way from the user's perspective is to describe the address x which will issue from the pipeline at the end of a given clock cycle. In the previous cycle, it would have been x−1 (i.e. during the current cycle, x−1 has just been removed from the pipeline). In the following cycle, it will be x+1 (i.e. during the next cycle, x will have been removed from the pipeline). Values of x≤0 represent initial cycles needed to fill the pipeline. An alternate way to know the state of the pipeline is by the pattern of subtubes that are not empty in a given cycle, which is what has been discussed earlier. The following analyzes the connection between the pattern of tubes that are not empty and the binary state x.

It is possible to analyze the state transitions independently of the tube contents M that are distributed among the subtubes $s_i$ and $c_i$. Let the non-boldface variable (with the additional subscript x) $s_{x,i}$ mean that the $s_i$ subtube is not empty corresponding to the binary state x of the pipeline. Similarly, the variable $c_{x,i}$ mean that the $c_i$ subtube is not empty corresponding to the binary state x and the variable $z_{x,i}$ mean that both subtubes are empty corresponding to the binary state x. The following recurrence describes in little-endian-zero-origin notation the pipeline state transition corresponding to x>1−aw:

$$s_{x,i} = \begin{cases} 0 & \text{if } i > aw \\ 1 & \text{else if } s_{x-1,i+1} \\ 1 & \text{else if } c_{x-1,i+1} \text{ and } f(x-1, i+1) \\ 0 & \text{otherwise} \end{cases}$$

$$c_{x,i} = \begin{cases} 0 & \text{if } i > aw \\ 1 & \text{else if } s_{x-1,i} \\ 1 & \text{else if } c_{x-1,i} \text{ and } \sim f(x-1, i) \\ 0 & \text{otherwise} \end{cases}$$

where $f(x,k)=(x+k)\equiv 0 \bmod 2^k$. If the x subscripts are eliminated above, and it is noted that the goal of logic 4000 in pipeline cycle x is to compute $f_i=f(x,i)$, those skilled in the art will also note that the state machine of FIG. 6 is similar (except FIG. 6 is optimized and allows for the force signal 5001 that lets the circuit cause the pipeline to jump to an arbitrary high-order address, rather than having to start at zero as the above recurrence does).

From this recurrence, we could display the evolution of the pipeline (left column of Table 1) visually using:

's' when $s_{x,i}$ indicates the ith pipeline stage is occupied by the "separate" subtube, 'c' when $c_{x,i}$ indicates the ith pipeline stage is occupied by the "combine" subtube, ' ' when $z_{x,i}$ indicates the ith pipeline stage has zero strands.

The algorithmic action of the pipeline is clearer with a slightly different notation (right column of Table 1):

'c' when $c_{x,i}$ indicates the ith pipeline stage is occupied by the "combine" subtube while simultaneously f(x,k) indicates a transfer (COMBINE operation) will occur, 'I' when $c_{x,i}$ indicates the ith pipeline stage is occupied by the "combine" subtube but the transfer does not occur

TABLE 1

Example Evolution of the Pipeline

| | | |
|---|---|---|
| −3 | s | s |
| −2 | sc | sI |
| −1 | scc | sII |
| 0 | sccc | sIII |
| 1 | cccc | ccII |
| 2 | s cc | s CI |
| 3 | cs c | cs I |
| 4 | sc c | sI I |
| 5 | cc c | cc C |
| 6 | s s | s S |
| 7 | csc | csI |
| 8 | scc | sII |
| 9 | ccc | ccI |
| 10 | s c | s C |
| 11 | cs | cs |
| 12 | sc | sI * |
| 13 | cc s | cc S |
| 14 | s sc | s SI |
| 15 | cscc | csII |

Analogous information is given in the table in FIG. 3, where the 'c' in left column of Table 1 corresponds to 01 in FIG. 3 and the 's' in the left column of Table 1 corresponds to 10 of FIG. 3. The upper-case letters and '*' in Table 1 highlight observations to be made later (and in this instance have nothing to do with little- or big-endian order). The goal of logic 4000 is to eliminate the integer x from the description of the state transition. We can imagine a function $x=X(s_0, \ldots s_{aw-1}, c_0, \ldots, c_{aw-1})$ that converts the current state of the pipeline into its associated integer, x, because each $0 \leq x < 2^{aw}$ corresponds to a unique pattern of these arguments, as illustrated in Table 1. It is not necessary to define X, but instead replace the difficult operation f(x,i) with $$f_k = f(X(s_0, \ldots s_{aw-1}, c_0, \ldots, c_{aw-1}), 1).$$

Note that the arguments may be truncated after the i−1 column (little-endian notation) because f(x,i) is a modulo-$2^i$ function, and we can overload the semantics of X so that the meaning is clear (the variables with subscripts >i are don't cares). Because of this cyclical pattern, the logic equations for $f_i$ may be obtained most easily by inspection of the tail of the state transitions, i.e., the line shown for $2^{aw}-i$ reveals the logic equation for as illustrated in Table 2 for aw=11. In Table 2, '.' is don't care, and 'z' is shown instead of ' ', and the left number is i, indicating the $f_i$ revealed by the pattern shown for $x=2^{aw}-i$.

TABLE 2

Transition for the tail of pipeline evolution for aw = 11

| i | x | |
|---|---|---|
| 10 | 2038 | szszzzzzzz . |
| 9 | 2039 | cscxzzzzzz . . |
| 8 | 2040 | sccxzzzzz . . . |
| 7 | 2041 | cccxzzzz . . . . |
| 6 | 2042 | szczzz . . . . . |
| 5 | 2043 | cszzz . . . . . . |
| 4 | 2044 | sczz . . . . . . . |
| 3 | 2045 | ccz . . . . . . . . |
| 2 | 2046 | sz . . . . . . . . . |
| 1 | 2047 | c . . . . . . . . . . |

Referring to FIG. 1, during normal operation (when force signal 5001, initialize signal 5002, freeze signal 5003 and flush signal 5004 are not asserted), only the low-order two bits of tube controls 1030, 1130, 1230, 1330, 1430 are relevant, because these indicate the three possible operations mentioned earlier: a) combining (without outputting); b) transferring (like a flip flop); and c) separating. Those skilled in the art will recognize other arrangements besides using the low-order two bit are possible. During normal operation (when signals 5001, 5002, 5003 and 5004 are not asserted), the logic 4000 will generate control tube control(s) 1030, 1130, 1230, 1330, 1430 that command the corresponding tube(s) 1010, 1110, 1210, 1310, 1410, . . . to perform separating operations if and only if the corresponding s-status signal(s) 1040, 1140, 1240, 1340, 1440 . . . is(are) asserted by the tube(s) in question during the current cycle. This has the effect that each of the s-status signals 1040, 1140, 1240, 1340, 1440 . . . is never asserted continuously for longer than one cycle during normal operation (it may be reasserted later, but never for longer than one cycle). Most of the time, the logic 4000 will generate control tube control(s) 1030, 1130, 1230, 1330, 1430 that command the corresponding tube(s) 1010, 1110, 1210, 1310, 1410, . . . to perform combining current contents with the output of the unit on the right (which, as just discussed, may have separated half its contents to give to the tube in question). Because this is the default, it is natural (but not required) to encode this behavior as 000 on each of tube control(s) 1030, 1130, 1230, 1330, 1430. In addition to a) combining and c) separating above, occasionally b) transferring is required. Every two raised to the bit-position cycles, the tube with that bit-position parameter needs to perform transferring its contents to the left, leaving the tube in question empty. The tubes do not have enough internal complexity (i.e., memory) to act as isolated binary counters, but the collective combination of the logic 4000 with the DNA tubes 1010, 1110, 1210, 1310, 1410, . . . communicating s-status signals 1040, 1140, 1240, 1340, 1440, . . . and c-status signals 1050, 1150, 1250, 1350, 1450, . . . back to the logic 4000 enable the logic 4000 to generate f-signals that assert the clock cycle in which such transferring should occur. The logic equations are given in Table 3, in terms of $c_i$, $s_i$ and $z_i = (\sim c_i)(\sim s_i)$, up to aw=32. The first few equations can be read from the example tail state transitions of Table 2. Cases for aw>32 are also possible: one of the C programs (pipeinc6xlogeqn.c) in appendix 3 may be used for this purpose.

TABLE 3

Logic equations $f_1 = c_0$
$f_2 = s_0 z_1$
$f_3 = c_0 c_1 z_2$
$f_4 = c_0 c_1 z_2 z_3$
$f_5 = c_0 s_1 z_2 z_3 z_4$
$f_6 = s_0 z_1 c_2 z_3 z_4 z_5$
$f_7 = c_0 c_1 c_2 z_3 z_4 z_5 z_6$
$f_8 = s_0 c_1 c_2 z_3 z_4 z_5 z_6 z_7$
$f_9 = c_0 s_1 c_2 z_3 z_4 z_5 z_6 z_7 z_8$
$f_{10} = s_0 z_1 s_2 z_3 z_4 z_5 z_6 z_7 z_8 z_9$
$f_{11} = c_0 c_1 z_2 c_3 z_4 z_5 z_6 z_7 z_8 z_9 z_{10}$
$f_{12} = s_0 c_1 z_2 c_3 z_4 z_5 z_6 z_7 z_8 z_9 z_{10} z_{11}$
$f_{13} = c_0 s_1 z_2 c_3 z_4 z_5 z_6 z_7 z_8 z_9 z_{10} z_{11} z_{12}$
$f_{14} = s_0 z_1 c_2 c_3 z_4 z_5 z_6 z_7 z_8 z_9 z_{10} z_{11} z_{12} z_{13}$
$f_{15} = c_0 c_1 c_2 c_3 z_4 z_5 z_6 z_7 z_8 z_9 z_{10} z_{11} z_{12} z_{13} z_{14}$
$f_{16} = s_0 c_1 c_2 c_3 z_4 z_5 z_6 z_7 z_8 z_9 z_{10} z_{11} z_{12} z_{13} z_{14} z_{15}$
$f_{17} = c_0 s_1 c_2 c_3 z_4 z_5 z_6 z_7 z_8 z_9 z_{10} z_{11} z_{12} z_{13} z_{14} z_{15} z_{16}$
$f_{18} = s_0 z_1 s_2 c_3 z_4 z_5 z_6 z_7 z_8 z_9 z_{10} z_{11} z_{12} z_{13} z_{14} z_{15} z_{16} z_{17}$
$f_{19} = c_0 c_1 z_2 s_3 z_4 z_5 z_6 z_7 z_8 z_9 z_{10} z_{11} z_{12} z_{13} z_{14} z_{15} z_{16} z_{17} z_{18}$
$f_{20} = s_0 c_1 z_2 z_3 c_4 z_5 z_6 z_7 z_8 z_9 z_{10} z_{11} z_{12} z_{13} z_{14} z_{15} z_{16} z_{17} z_{18} z_{19}$
$f_{21} = c_0 s_1 z_2 z_3 c_4 z_5 z_6 z_7 z_8 z_9 z_{10} z_{11} z_{12} z_{13} z_{14} z_{15} z_{16} z_{17} z_{18} z_{19} z_{20}$
$f_{22} = s_0 z_1 c_2 z_3 c_4 z_5 z_6 z_7 z_8 z_9 z_{10} z_{11} z_{12} z_{13} z_{14} z_{15} z_{16} z_{17} z_{18} z_{19} z_{20} z_{21}$
$f_{23} = c_0 c_1 c_2 z_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22}$
$f_{24} = s_0 c_1 c_2 z_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23}$
$f_{25} = c_0 s_1 c_2 z_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24}$
$f_{26} = s_0 z_1 s_2 z_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25}$
$f_{27} = c_0 c_1 z_2 c_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25} z_{26}$
$f_{28} = s_0 c_1 z_2 c_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25} z_{26} z_{27}$
$f_{29} = c_0 s_1 z_2 c_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25} z_{26} z_{27} z_{28}$
$f_{30} = s_0 z_1 c_2 c_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25} z_{26} z_{27} z_{28} z_{29}$
$f_{31} = c_0 c_1 c_2 c_3 c_4 z_5 z_6 z_7 z_8 z_9 z_{10} z_{11} z_{12} z_{13} z_{14} z_{15} z_{16} z_{17} z_{18} z_{19} z_{20} z_{21} z_{22} z_{23} z_{24} z_{25} z_{26} z_{27} z_{28} z_{29} z_{30}$ The controller 5000 issues flush signal 5004 to the logic 4000 and to the comparison unit 2000 when it wishes all strands to be returned to memory tube 3000. The controller 5000 needs this to be completed prior to the sequence of steps required for random accessing of an arbitrary binary starting address. When flush signal 5004 is issued, logic 4000 generates 3-bit tube controls 1030, 1130, 1230, 1330, 1430, . . . corresponding to the respective DNA tubes 1010, 1110, 1210, 1310, 1410, . . . that cause DNA tubes 1010, 1110, 1210, 1310, 1410, . . . to empty all the DNA strands they contain via pipes 1020, 1120, 1220, 1320, 1420, . . . Also, when flush signal 5004 is issued, comparison unit 2000 empties all the DNA strands it contains via pipe 2309. The DNA strands in pipes 300, 2309, 1020, 1120, 1220, 1320, 1420, . . . are combined together into pipe 3020 and transferred into memory tube 3000. This may take one or more clock cycles to accomplish depending on implementation details. In addition to when flush signal 5004 is issued, pipe 3020 transfers DNA strands back to memory tube 3000 when the processing unit 100 is done with them; when the comparison unit 2000 have filtered them out (because they don't match the starting-address); or when the controller 5000 issues the force signal 5001. This latter case, when then controller issues the force signal 5001, is part of sequence of steps required for random accessing of an arbitrary binary starting address.

The complete sequence of steps required for random accessing of an arbitrary binary starting address is as follows: 1. The controller 5000 issues flush signal 5004 to the logic 4000 and to the comparison unit 2000 so that all DNA strands will be returned to memory tube 3000. 2. The controller waits (if necessary) the proper number of cycles for this to be completed. 3. The controller 5000 issues initialize signal 5002 to comparison unit 2000, along with desired-starting-address low-order bits 5010, 5011, 5012, ..., so that comparison unit 2000 is prepared to filter out strands that do not match the desired-starting-address low-order bits 5010, 5011, 5012, ... The initialize signal 5002 also causes memory tube 3000 to transfer its contents via pipe 1560 to the adjacent tube, which in the five-bit example of FIG. 1. is tube 1410. 4. For aw minus ceil(log$_2$(aw)) cycles (in the example of FIG. 1 of aw=5, this would be two cycles), the controller issues the force signal 5001 when the corresponding high-order bit position of the desired starting address is '1' (in the example of FIG. 1, during the first cycle force is asserted if and only if the highest-order bit of the address is '1'; during the next cycle force is asserted if and only if the next highest-order bit of the address is '1'); asserting force changes the way separating happens (those strands whose corresponding bit position are '0' are returned to the memory tube 3000 ultimately via pipe 3020 whereas those DNA strands whose corresponding bit positions are '1' are moved leftward in the pipeline). 5. The controller allows normal initialization of the pipeline with force unasserted for ceil(log$_2$(aw)) cycles (in the example of FIG. 1, three cycles), so that at the moment strands start flowing out of pipe 1060, this has the effect of accessing the address whose low-order bits are 000 ... which is the reason for the comparison unit 2000. 6. The comparison unit 2000 discards (via pipe 2309) strands input via pipe 1060 until it finds a strands whose low-order address bits match desired-starting-address low-order bits 5010, 5011, 5012, ... 7. Finding such a strand alters the state of the comparison unit 2000 so from that moment onward comparison unit 2000 passes through (to pipe 200) all strands input via pipe 1060. 8. From this time onward (until the controller 5000 decides to initiate random access again), the natural operation of the pipeline 1000 will cause one DNA strand (i.e. redundant copies of that strand) to be transferred via pipe 200 to processing unit 100 every cycle. Because sometimes processing unit 100 may need more than one cycle to process a strand, the controller 5000 may issue freeze signal 5003, which causes all components inside pipeline 1000 to maintain their current state, giving as much extra time to processing unit 100 as controller 5000 wishes to grant.

Figure 2:
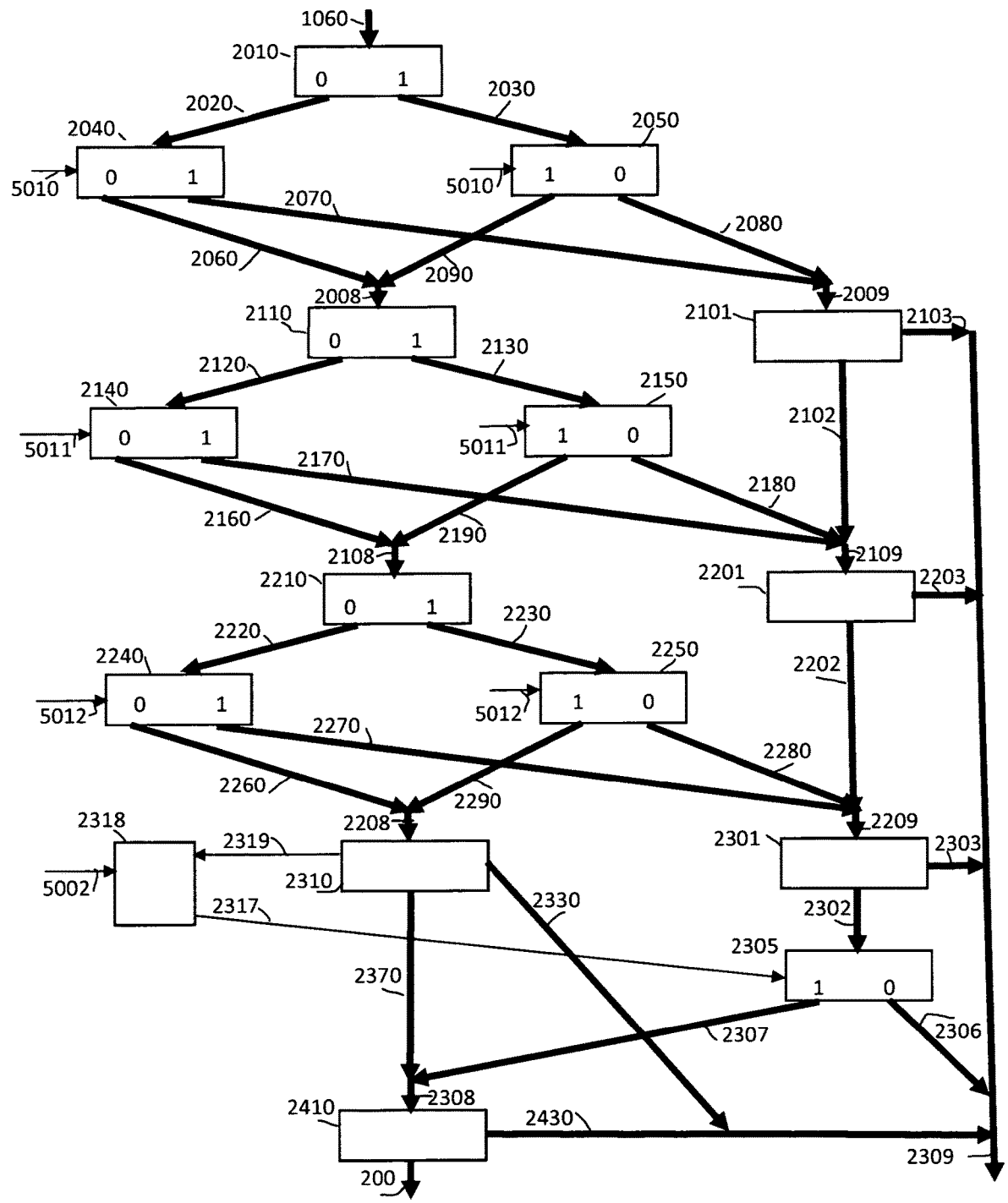
FIG. 2 shows the optional compare unit.

Referring to FIGS. 1 and 2, the comparison unit 2000 includes tubes 2010, 2110, 2101, 2210, 2201, 2310, 2301 and 2410 as well as demultiplexers 2040, 2050, 2140, 2150, 2240, 2250 and 2305. Comparison unit 2000 also includes state machine 2318, whose initial state is established by initialize signal 5002. The pipe 1060 is input to comparison tube 2010, which is configured to act as a separating tube based on the least-significant-address bit of its input strands, with output pipes 2020 (with strands whose bit is '0') and 2030 (with strands whose bit is '1'). Pipe 2020 is input to demuxiplexer 2040 which transfers these strands either to pipe 2060 or to pipe 2070 based on the least-significant-starting-address bit 5010. Pipe 2030 is input to demuxiplexer 2050 which transfers these strands either to pipe 2090 or to pipe 2080 based on the least-significant starting address bit 5010. Pipes 2060 and 2090 are combined into pipe 2008. Pipes 2070 and 2080 are combined into pipe 2009. The net effect is that strands whose low-order address bit matches the least-significant starting address bit 5010 are transferred into comparison tube 2110, while those that don't are transferred into reject tube 2101, whose output is pipe 2102.

Tube 2110 is configured to act as a separating tube based on the next-significant-address bit of its input strands, with outputs pipes 2120 (with strands whose bit is '0') and 2130 (with strands whose bit is '1'). Pipe 2120 is input to demuxiplexer 2140 which transfers these strands either to pipe 2160 or to pipe 2170 based on the next-significant-starting-address bit 5011. Pipe 2130 is input to demuxiplexer 2150 which transfers these strands either to pipe 2190 or to pipe 2180 based on the next-significant-starting-address bit 5011. Pipes 2160 and 2190 are combined into pipe 2108. Pipes 2102, 2170 and 2180 are combined into pipe 2109. The net effect is that strands whose next-significant address bit matches the next-significant-starting-address bit 5011 are transferred into comparison tube 2210, while those that don't are transferred into reject tube 2201, whose output is pipe 2102 (which also has those that did not match the earlier stage).

Tube 2210 is configured to act as a separating tube based on the further-significant-address bit of its input strands, with outputs pipes 2220 (with strands whose bit is '0') and 2230 (with strands whose bit is '1'). Pipe 2220 is input to demuxiplexer 2240 which transfers these strands either to pipe 2260 or to pipe 2270 based on the further-significant-starting-address bit 5012. Pipe 2230 is input to demuxiplexer 2250 which transfers these strands either to pipe 2290 or to pipe 2280 based on the further-significant-starting address bit 5012. Pipes 2260 and 2290 are combined into pipe 2208. Pipes 2202, 2270 and 2280 are combined into pipe 2209. The net effect is that strands whose further-significant address bit matches the further-significant-starting-address bit 5012 are transferred into reject tube 2310, while those that don't are transferred into reject tube 2301 (which also has those that did not match the earlier stages).

At this stage, tube 2310 contains strands that match the starting-address bits 5010, 5011 and 5012, while tube 2301 contains those that do not. Signal 2319 indicates whether tube 2310 is empty or not. If signal 2319 indicates tube 2310 is empty, state machine 2318 does not change its state (the initialize signal 5002 created this state at the beginning). If signal 2319 indicates tube 2310 is not empty, state machine 2318 changes to the non-initial state. The flag output 2317 of state machine 2318 reflects its current state, and controls demultiplexer 2305. If flag 2317 indicates the state machine 2318 is still in the initialize state, demultiplexer 2305 transfers strands from pipe 2302 onto pipe 2306, where they will be combined into pipe 2309 and recycled back to the memory tube 3000. In other words, if state machine 2318 is still in the initialize state, such strands will not be output by the comparison unit 2000. On the other hand, if flag 2317 indicates the state machine 2318 is no longer in the initialize state, demultiplexer 2305 transfers strands from pipe 2302 onto pipe 2307 which is combined with pipe 2370. This means the one DNA strand that matched the low-order-starting address on pipe 2370 and all DNA strands that follow in later cycles on pipe 2307 will be transferred into tube 2410, whose output pipe 200 connects to processing unit 100.

During the first cycle the flush signal 5004 is asserted, tubes 2101, 2201, 2301, 2310 and 2410 empty their contents via pipes 2103, 2203, 2303, 2330 and 2430, respectively. Pipes 2306, 2103, 2203, 2303, 2330 and 2430 are combined into pipe 2309 and recycled back to the memory tube 3000. Tubes 2010, 2110 and 2210 are using both of their outputs for other purposes, and are not emptied by the flush signal 5004. (Here there are three such tubes; in general there would be log$_2$(aw) such tubes.) Instead strands in those tubes 2010, 2110 and 2210 travel naturally through the pipeline until they arrive at one of the other tubes 2101, 2201, 2301, 2310 and 2410. This means, as suggested earlier, it takes multiple cycles to flush the pipeline. The specific example of FIGS. 1 and 2 requires that the flush signal 5004 is asserted for four cycles; in general, this would be $\log_2(aw)+1$ cycles.

Applications of the Present Invention

One application of the present invention is to store instructions for processor 100 when it is a biochemical processor that executes machine language. Most conventional electronic processors use a Random Access Memory (RAM) in which the address is not recorded with the contents. Typically, such machines have two distinct registers: a program counter (PC) that provides the address, and an Instruction Register (IR) which holds a copy of the current instruction associated with that PC. Instead, the present invention acts like a Content Addressable Memory (CAM), where contents and address are both recorded on each strand. The role of the PC and IR have been merged into a single PCIR tube, another name for $t_{-1}$ (provided by pipe 200 to processor 100), which holds a single strand on which both an instruction and its associated address within the larger program are encoded. Control flow is implemented by choosing one instruction/address strand from many in a Memory (M) tube and moving that strand to the PCIR, after first transferring the old strand from the PCIR back to M, which is the natural operation of the pipeline in the present invention. During normal execution, no new machine-language strands are created, copied or destroyed; they simply cycle in and out of the PCIR following the flow of control of the program.

The following shows instructions for a one-address machine, using two accumulator tubes $a_0$ and $a_1$, where an address field specifies a bit address for some instructions (SET1 and SEPARATE1) and a tube address (in the user tubes $u_i$) for other instructions (variations of combine that transfer into and out of the accumulator tubes). The one-address ISA could be emulated by the following:

COMBINE0(t) {COMBINE($a_0$, t);}
SEPARATE1(i) {SEPARATE($a_1$, $a_0$, i);}
SET1(i) {SET($a_0$,i);}
COMBINE1(t) {COMBINE(t, a0); COMBINE(a0, a1);}

The COMBINE0 instruction plays the role that an arithmetic instruction plays in a conventional one-address ISA. Two accumulator tubes are needed because SEPARATE1 assumes these rather than allowing the user to specify them in software. The two accumulator tubes act like a tiny stack, with COMBINE1 playing the role of a store/pop instruction that transfers $a_1$ to $a_0$ after combining the old $a_0$ into the t specified by the user tube address. The following suggests the type of operations that processing unit 100 performs after the comparison unit 2000 has delivered the instruction to PCIR:

fetchExecute1( )
{SEPARATE(temp,PCIR, iw−2);
  SEPARATE(temp,PCIR, iw−1);
  if (!EMPTY(temp))
    CAMinst( );
  else
    execute1( );
  COMBINE(M, PCIR);
}

The constant iw is the instruction width, including the aw bits that specify the address. If the two most-significant bits (iw−1 and iw−2) are both zero, a non-CAM instruction is executed. If either of these bits are one (meaning the PCIR has moved to temp), CAMinst handles cases like jump instructions (which trigger a pipeline initialization). The one-address non-CAM instruction is handled simply by execute1, based on previously established contents of $a_0$ and $a_1$:

execute1( )
{computeOp( );
  decoder(3); //eight tubes or bits of data
  for (i=0; i<8; i=i+1)
  {if (!EMPTY($d_i$))
    {if (op==0) INIT($a_0$);
    if (op==1) SET($a_0$, i); //SET0
    if (op==2) SEPARATE($a_1$, $a_0$, $a_0$, i); //SEPARATE0
    if (op==3) COMBINE($a_0$, $u_i$); //COMBINE0
    if (op==4) {COMBINE($u_i$, $a_0$); COMBINE($a_0$,$a_1$);}//
      COMBINE1
    . . .
  }}
  unDecoder(3);
}
decoder(n)
  (COMBINE($d_0$, PCIR);
    for (i=0; i<n; i=i+1)
      {for (j=0; j<=(1<<i)−1; j=j+1)
        SEPARATE ($d_{(1<<i)+j}$, $d_j$, $d_j$, i+aw);
  }}
  unDecoder(n)
    {for (i=0; i<(1<<n); i=i+1)
      COMBINE(PCIR, $d_i$);
    }

First, computeOp copies bits that identify the operation from PCIR into a controller variable op. Calls to decode and unDecode determine the bit or tube address. After decode, one of eight (in this example) $d_i$ tubes contains the instruction; which tube is not empty determines the value of i. Using computeOp simplifies the controller and allows the code to say things like (op==2), but the decoder approach could be used there also. COMBINE1 and COMBINE0 reference user tubes, $u_i$. Although it takes two "COMBINE" operations to specify op=4, these may execute in parallel (as illustrated by the general tube module of the Verilog code in Appendix 1) allowing the pipeline to proceed without freezing, because every possible non-CAM instruction executes in one cycle. The unDecoder operation combines the $d_i$ tubes, which allows the instruction strand which was in one of them to be returned to M. The CAM instructions, on the other hand, require the pipeline to freeze and/or initialize.

Another application of the present invention is using DNA as a replacement for a disk drive. The information is stored on multiple strands with unique addresses. Just as a disk drive slowly seeks a sector to provide random access, followed by a fast sequential read of contiguous blocks of data, the present DNA memory hierarchy initializes its pipeline (requiring about aw cycles) to access the first set of stands, followed by fast sequential access. Electrochemical sampling a portion of the addressed strands using technology such as a nanopore sensor allows the information encoded on the strand to be converted to electronic information, which can be stored in a conventional electronic memory for further processing. Assuming redundancy and error coding is used, the recovered information in the electronic memory can be corrected for errors. Although the concept of a DNA disk is not new, the present invention makes it more feasible to implement because it allows fast bursts of data transfer after random access. In contrast, the prior art (such as Milenkovic et al., Kashiwamura et al.) provides random access by slow PCR (requiring many cycles) to provide selective amplification of the strands to be accessed. In the prior art, to continue reading sequentially after electrochemically converting the first set of strands requires additional PCR, whereas the present invention can process one addressed set of strands per cycle. Furthermore, unlike addressing by PCR, which contaminates and/or dilutes the supply of memory strands, the present invention does not modify, change or destroy any memory strands.

Referring to FIG. 7, a DNA disk drive is substantially similar to the generic memory hierarchy of FIG. 1, except the role of the controller 5000 is carried out by an electronic computer 5100 attached to an electronic memory 5200 via bus 5101. Those skilled in the art will realize other computer architectures involving processor(s) and memory(ies) are possible. In addition to implementing the algorithms to control the DNA memory hierarchy, this electronic computer 5100 has an operating system and user applications that initiate access to data stored in the DNA strands. The force 5001 and init 5002 signals are generated by the electronic computer 5100 according to the methods described earlier involving high order bits, in response to the operating system and/or user application requirements. The processor 100 is an electrochemical device, such as a nanopore sensor or sequencer, that can recover information from samples of individual DNA strands provided via by pipe 1060. The sampling action is under the control of electronic computer 5100 via control bus 5102. After sampling, the strands are returned via pipe 300 to memory (M) tube 3020. The information encoded on the strand is recovered as electronic information and stored into electronic memory 5200 via bus 5201. The electronic computer 5100 determines the number of pipeline cycles for which the sampling and storing occurs, and is able to manipulate the electronic information recovered from the strands, for example, implementing error correction, file systems, etc.

Description of the Appendices

In order to fully describe and simulate the system described by FIGS. 1 and 2, Appendix 1 gives a Verilog hardware description language code for the pipelined DNA memory hierarchy 1000. The Verilog code uses little-endian-zero-origin notation ($t_0$-$t_4$ in FIG. 1). The source code includes comments with reference numerals that correspond to elements of FIGS. 1 and 2. Since Verilog is a language primarily designed to describe electronic hardware, it takes some effort to simulate the essential properties of a biochemical system, which is encapsulated mostly into the modules "tube" and "demux" given at the start of the source code. In particular, the code uses wires of size ['NUMST* (1(+1)–1:0], where 'NUMST is the maximum number of strands ever allowed in a tube or pipe, and 'K is the total number of bits (including the aw address bits) per strand. The 'K+1 is because the simulation uses an additional bit to indicate the existence of a strand. It is easy (and often necessary) in electronic information processing to create copies of information. This is different than biochemical processing, in which the DNA strand is only moved but not created, copied or destroyed (at least within the scope of this invention). The many functions of module "tube", such as "combine", help encapsulate this behavior, although internally it is necessary to create many copies of the information representing a DNA strand. The end user perceives only one copy of each strand, which moves through different tubes as the simulation progresses. In particular, the three "always" blocks that compute "t", "o1" and "o2" (the tube's internal contents, and its two outputs) insure that each particular strand ends up in only one of these variables, even though electronic copies are made to arrive at this end result. The "case" statements inside these "always" blocks define a truth table for the operation of the 3-bit tube controls 1030, 1130, 1230, 1330, 1430, . . . mentioned earlier. Those skilled in the art will recognize this is just an example implementation, and many other ways to achieve equivalent operation are possible. In particular, many kinds of specialized tubes that would not need three control bits could be used instead of one general-purpose "tube" module as given here to shorten the Verilog coding.

The natural operation of the pipeline may be described by a recursive function, which is given in C code in Appendix 2. A concise definition of this function is:

$$m(x, k) = \begin{cases} \emptyset \text{ if } k > aw \\ inm(0, k, st, M) \text{ else if } x \leq st \\ L(m(x-1, k+1)) \text{ else if } |m(x-1, k+1)| > 1.5r2^k \\ m(x-1, k+1) \text{ else if } f(x-1, k+1) \\ m(x-1, k) \text{ else if } \sim f(x-1, k) \\ H(m(x-1, k), k) \text{ else if } |m(x-1, k)| > 1.5r2^{k-1} \\ \emptyset \text{ \& otherwise} \end{cases}$$

where the boldface m indicates the function returns a sets of strands, the function H(m,k) returns a set of strands of higher values (with bit k set, in other words half of the separate operation), the function L(m,k) returns a set of strands lower values (with bit k cleared in other words the other half of the separate operation), inm gives initial values, and |m| measures the number of strands compared against $3n'4=1.5r2^{k-1}$. The non-tail recursion of this definition makes it inefficient to run, but it is a compact description of how the pipeline works, and it allows mathematical reasoning about its operation. It is closely tied to the definition of $s_i$ and $c_i$. The C program uses a bit set internal representation. Because of the limitations of C long long, it can only simulate tubes with no more than 64 strands. Like the Verilog code, it makes multiple copies of its internal representation, even though in the biochemical system only one copy exists.

Appendix 3 gives several C programs that print "s"/"c" patterns for the DNA memory hierarchy similar to Table 2, including one (pipeinc6xlogeqn.c) with outputs them in a logic-equation form similar to Table 3. Together these demonstrate the essential logical correctness of the present invention without having to simulate at the strand level. The first program, pipeinc1.c, is an early version (DNA23 poster) using a parametric equation in little-endian-one-origin (to avoid mentioning Li). The next program (pipeinc2x.c) introduces the variable x mentioned earlier. The next (pipeinc3x.c) changes to zero origin notation for consistency with this specification. The next three (pipeinc3xfun . . . pipeinc5xfun.c) use f(x,i). The next two (pipeinc6xfunsc.c and pipeinc6xlogeqn.c) use the recurrence for $s_i$ and $c_i$, which shows the validity of the ASM chart in FIG. 5 and the state machine in FIG. 6. Logic (like Table 3) replaces f(x,i) in pipeinc7xfunsc.c. Finally, initialization via the force signal 5001 is given in pipeinc8xfunsc.c, which shows random access (3 bits in this code for a 4- or 5-bit address) works properly.

Appendix 4 gives a Java class that simulates the full memory hierarchy (including compare unit 2000, and associated high-order-bit initialization) for all possible random access cases. In other words, there are 2048 random accesses, many of which require (up to 15) extra cycles for the compare unit 2000 to discard the extra strands that come before the start of the desired address. For each of these cases, the rest of memory from that point to 2047 is accessed. In other words, the simulation makes about $2^{21}$ sequential accesses producing significant output, proving that the initialization, compare unit 2000 and logic 4000 work for every possible case. There are two initialization approaches that can be used, depending on which method is called at the line with the "***" comment: a) like the Verilog code of Appendix 1, using precisely the aw–ceil ($\log_2$(aw)) bits as the high-order address (Java method is fetchpipeplay2), and b) for certain addresses recognized by Java method fetchpipeplay, use additional high-order bits to reduce the extra cycles needed for random access. The Java code also computes the average number of extra cycles (beyond the aw=11 needed for pipeline initialization): a) 7.5625 and b) 2.0957. The hardware of FIG. 1** is compatible with either approach. The DNA sticker simulation was translated from the JavaScript sticker simulator at http://www.xlnsresearch.com/sticker1.htm.

There are many options to enable arbitrary random access to the pipeline, and the following explains the background behind the options discussed above. A naive implementation would simply iterate the pipeline start times. On average, this would take $2^{aw-1}$ iterations, which is much too slow. Recall x=X($s_0, \ldots s_{aw-1}, c_0, \ldots, c_{aw-1}$). Because there is a one-to-one mapping between the pattern of $s_{x,i}$ and $c_{x,i}$ variables and a given $0 \leq x < 2^{aw}$, an inverse function exists:

$$X^{-1}(x) = (s_{x,0}, \ldots s_{x,aw-1}, c_{x,0}, \ldots, c_{x,aw-1})$$

Random access to an address, start, simply means initializing the pipeline state to $X^{-1}$(start). One idea would be to force all tubes into the correct state based on the bits of the entire address, which, surprisingly, we will see by itself will not quite work in every case, but which provides a foundation. Below on the left is code for fetchpipe to initialize $c_i$ and $s_i$ subtubes tubes. It uses Sakar-Ghosal probing of individual bits of a strand contained in an addr tube and a temp tube to sense the value of the bit (so the target address is on a strand which would be useful when the memory hierarchy is part of a totally biochemical processor executing a machine language branch instruction on the strand), but the details being explained may be lost in the use of a temp tube. For clarity, similar code, fetchpipestart, on the right uses an integer variable, start, to indicate the same thing, and for which the probing of its bits is done with conventional masking. The fetchpipestart approach is closer to an implementation of a DNA disk drive attached to a conventional electronic computer that would issue start, and receive the equivalent electronic information from the addressed strands. What matters for understanding the pipeline initialization is that the COMBINEs and SEPARATEs are identical in both functions.

```
fetchpipe(addr,temp)                fetchpipestart(start)
{ combine (s_{aw-1},M);             {combine (s_{aw-1},M);
  for (i=aw-1; i>0; i=i-1)           for (i=aw-1; i>0; i=i-1)
  {SEPARATE(temp,addr,addr,i+aw);   {
    if (!ISEMPTY(temp)) if (((1<<i)&start) !=0)
      SEPARATE(s_{i-1},M,s_i,i);       SEPARATE(s_{i-1},M,s_i,i);
    else                              else
      SEPARATE (c_i,s_{i-1},s_i, i);    SEPARATE (c_i, s_{i-1},s_i, i);
  combine(addr,temp);
  } }
  SEPARATE(temp,addr,addr,i+aw);
```

```
    if (!ISEMPTY(temp)) if ((1&start) !=0)
      SEPARATE (c_0,M,s_0,0);  SEPARATE(c_0,M,s_0,0);
    combine(addr,temp);
} }
```

Address bit 0 is not processed inside the for loop. Instead, there is a later if statement that only does something for odd addresses. Let's consider the case that start is zero. Since every bit is zero, each time through the loop the SEPARATE after the else causes $c_i$ to get H($s_i$,i) and $s_{i-1}$ to get L($s_i$,i). In other words, among the s subtubes, only $s_0$ is not empty, and among the c subtubes only $c_0$ is empty. This matches the first four lines of Table 1. Next, let's consider start=1. This is similar, except the if statement dealing with odd addresses causes a further SEPARATE so that all s subtubes are empty and all c subtubes are not empty, which matches the x=1 line of Table 1. Finally, consider when start is a power of two. On the ith iteration, the SEPARATE after the if causes the unneeded lower-valued strands (that proceed start) from the ith subtube (L($s_i$,i)) to be returned to M (rather than stay in the pipeline) and the remaining higher-valued strands (H($s_i$,i)) to be moved into subtube $s_{i-1}$. This leaves both $s_i$ and $c_i$ empty.

In order to know whether fetchpipestart works, we can initialize the pipeline and check whether it outputs all strands sequentially from start to $2^{aq}-1$. A slightly modified version of the Java simulator in Appendix 4 has tested cases up to aw=32 which verify that fetchpipestart sometimes works, for values of start such as 0, 1, 2, 4, 5, 8, etc. It also works for powers of two. Unfortunately, fetchpipestart by itself fails to work for cases like 3, 6, 7, 11, 13, 14, 15, etc. In these situations, the pipeline starts to output the first expected strands, but then freezes. This happens because higher tubes have not been prepared with the proper contents. The upper-case letters and '*' in Table 1 show how the pipeline prepares these tubes during its normal evolution. (The '*' shows where a 'C' would have been if aw had been larger.) When we use fetchpipestart, we are jumping over that evolution. For some cases (like powers of two), fetchpipestart just happens to put the pipeline in the same state that the slow evolution from 0 to start would cause. But for cases on a line immediately after one of the upper-case letters or '*' in Table 1, fetchpipestart makes a mistake. These are on lines 2, 5, 6, 10, 12, 13, 14, . . . The failed values of start are always one more than the number of these lines. (These patterns hold not just for the small example in Table 1, but in exhaustive simulations too extensive to reproduce here.) The upper case 'C's and 'S's, proceeded by one or more spaces, are bringing higher-valued strands into lower-numbered tubes where they will be needed in only a few clock cycles. There is a mathematical pattern that allows us to recognize the set of values 3, 6, 7, 11, 13, 14, 15, . . . which cause this problem. These cases satisfy $$2^{nN+1} - nN \leq \text{start} \mod 2^{nN+1},$$

where $1 < nN \leq aw-2$ is the upper bound on the number of extra operations needed to correct the problem. We can think of the largest value that satisfies this as being a function of start. Computing nN(start) requires bit-wise operations as well as addition and comparison:

```
getnN(int start)
{ int i,nN;
  nN=0;
  for (i=1; i<=aw-2; i++) //don't do MSB
  { if ((1<<(i+1))-i <= (((1<<(i+1))-1) &start) )
      nN=i;
  }
  return nN;
}
```

More abstractly, for an argument $0 \leq x < 2^{aw}$, there are several useful properties of nN(x): First, nN(x)≤aw−2 because it is defined this way. If nN(x)≠0, there exists an iN≤nN(x) such that nN(x−iN). Also, for all integers $0 \leq i < 2^{aw-ceil(\log_2(aw))}$, $nN(i2^{ceil(\log_2(aw))})=0$. Values of start for which nN(start)=0 are exactly the cases where fetchpipestart works by itself, which is the reason the embodiment of the present invention given in FIGS. 1 and 2 initializes using aw−ceil($\log_2$(aw)) high-order bits of the address.

A cheaper alternative (which would eliminate the need for comparison unit 2000 in the context of a biochemical processor where the pipeline is only being used to fetch instructions, and the initialization problem only arises with branch instructions) would do the calculation of nN during compilation, and insert NOPs into the object code generated by the compiler such that the target of all branch addresses satisfy nN=0. This is possible because each region in which nN>0 is preceded and followed immediately by a region in which nN=0. This compile-time alternative would increase code size, and decrease speed of a compiled program that will depend on the properties of the individual program being compiled. Every target address would be preceded by a variable number of NOPs that would not have been needed for a processor with correct hardware pipeline initialization as provided by FIGS. 1 and 2. The cost effectiveness of this alternative requires empirical study using actual source software applications, but a rough guess based on nN<aw=20 and ten percent of those $2^{20}$ addresses as potential branch targets is that the compile-time alternative might double program size and half performance (each of the targets on average needs aw/2=10 NOPs, and the ten percent of the original program which contains the targets then will take roughly as much memory as the rest of the non-target part of the program).

In the context of a DNA disk drive, it may be reasonable to require all random access to use only aw−ceil($\log_2$(aw)) high-order bits, thereby eliminating the need for comparison unit 2000. This would be analogous to seeking a sector (or a track) on a mechanical drive, and then reading several blocks sequentially, where the stride of access for the present invention would be $2^{ceil(\log_2(aw))}$.

The idea of random access by iterating start times is exponentially slow, but trying to arrive directly at the pipeline state for every case of start is difficult when nN(start)≠0. FIGS. 1 and 2 take a compromise approach which brings the pipeline to a state close to start, and then iterates for a handful of cycles. Extra comparison hardware 2000 filters those first few strands (whose addresses are <start) from being output by the pipeline; later strands pass through this extra hardware. The approach described earlier masks the low-order ceil($\log_2$(aw)) bits of start and then forces the pipeline to count up from that address to start before the extra comparison hardware allows strands through. The first aw cycles initialize the pipeline to the masked value of start. Then the comparison hardware 4000 ignores the strands whose address is less than start. In order to do this, it need to remember those low-order bits as controller variables 5010, 5011, 5012 . . . (st[3] . . . st[0] in the code). For 9≤aw≤16, masking the low four bits means at most 15 extra cycles before the desired strands begin flowing out of the pipeline one per cycle. Assuming the low-order bits of start are uniformly distributed, this would be an average of about 7.5 extra cycles allowing access for up to 64K strands. (Masking the low-order 5 bits increase the average time to 15.5 allowing access to 4G strands.) Here are slightly modified versions of fetchpipe that implements masking of the low-order four bits:

```
fetchpipe4(addr,temp)          fetchpipe4(addr,temp)
{ combine (s_{aw-1},M);         {combine (s_{aw-1},M);
  for (i=aw-1; i>4; i=i-1)       for (i=aw-1; i>4; i=i-1)
  {SEPARATE(temp,addr,addr,i+aw);   { SEPARATE
                                    (temp,addr,addr,i+aw);
   if (!ISEMPTY(temp)) force=!ISEMPTY(temp);
       SEPARATE (s_{i-1},M,s_i,i);
   else pipecycle( );
       SEPARATE (c_i,s_{i-1},s_i,i);
   combine(addr,temp);          combine(addr,temp);
  } }
  force=0;
  for (i=3; i>=0; i=i-1)         for (i=3; i>=0; i=i-1)
  {SEPARATE(temP,addr,addr,i+aw);   { SEPARATE
                                    (temP,addr,addr,i+aw);
   st[i]=!ISEMPTY(temp);        st[i]=!ISEMPTY(temp);
   combine(addr,temp);          combine(addr,temp);
       SEPARATE(s_{i-1},M,s_i,i);
   if (i>0)
       SEPARATE (c_i,s_{i-1},s_i,i);
  } }
} }
```

The one on the left (fetchpipe4) uses SEPARATEs analogously to fetchpipe (and is very similar to fetchpipeplay2 in Appendix 4); the one on the right uses the force approach shown in FIGS. 1 and 2 (and is similar to how the Verilog code in Appendix 1 operates). The advantage of the force approach is that the datapath for $s_i$ and $c_i$ can be fixed based on a simple nearest-neighbor pattern without needing general-purpose sticker operations referencing arbitrary tubes. Although such general-purpose operations are needed elsewhere in a universal biochemical sticker processor capable of executing machine language instructions, other applications, like a DNA disk drive, do not need such generality. Being able to eliminate them in the memory hierarchy improves its efficiency.

A faster alternative is possible for random access. The masking of the low ceil($\log_2$(aw)) bits of start can be thought of as computing iN=start mod $2^{ceil(\log_2(aw))}$ which will guarantee nN(start−iN). Masking is a simple operation, but it ignores that smaller values of iN might suffice, which could be a compromise between masking and the optimum. Table 4 shows a selective masking scheme which is a better compromise, and that is compatible with the hardware of FIG. 2. When fetchpipeplay (in Appendix 4) implements this for 9≤aw≤16, the overall average pipeline initialization latency (including comparison unit 2000) is about six cycles faster than simple masking.

TABLE 4

Selective masking of start avoids masking in most cases when nN(start) = 0.

| | | | |
|---|---|---|---|
| . . . . . . . . . . . . . .01x | [2, 3] | => | 2 |
| . . . . . . . . . . . . .01xx | [4, 7] | => | 4 |
| . . . . . . . . . . . .011xx | [12, 15] | => | 12 |
| . . . . . . . . . . .011xxx | [24, 31] | => | 24 |
| . . . . . . . . . .0111xxx | [56, 63] | => | 56 |
| . . . . . . . . .01111xxx | [120, 127] | => | 120 |
| . . . . . . . .011111xxx | [248, 255] | => | 248 |
| . . . . . . .0111111xxx | [496, 511] | => | 496 |
| . . . . . .0111111xxxx | [1008, 1023] | => | 1008 |
| . . . . .01111111xxxx | [2032, 2047] | => | 2032 |
| . . . .011111111xxxx | [4080, 4095] | => | 4080 |
| . . .0111111111xxxx | [8176, 8192] | => | 8176 |
| .01111111111xxxx | [16368, 16384] | => | 16368 |
| 011111111111xxxx | [32752, 32768] | => | 32752 |

Selective masking occurs when a zero is followed by a group of ones immediately before the masked bits (denoted by 'x'); the number of masked bits depends on where the group of ones start. The decimal intervals beside each mask describe the first such case where the rule applies; the number after "⇒" is the decimal value that all values within the interval are mapped into; don't cares ('.') encompass many other cases. Note that all cases (3, 6, 7, 11, 13, 14, 15 . . . ) that fail without masking are included within one of the intervals (when don't cares are also considered, as 11 is $1011_2$, which is the "0.01 x" case).

CONCLUSIONS, RAMIFICATIONS AND SCOPE

Accordingly, the reader will understand the pipelined DNA memory hierarchy provides random access to a high-order address, using the pipeline initialization techniques disclosed without having to use enzymes, synthesize probe molecules or perform PCR at access time. Also, the reader will understand the pipeline then provides fast access to sequential addresses each cycle thereafter. Such properties make such embodiments desirable for several applications, including, but not limited to, execution of machine language instructions and reading of successive blocks of data from a file.

Although the description above contains many specificities, these should not be construed as limiting the scope of the embodiments but as merely providing illustrations of some of several embodiments. For example, the testing of whether the subtubes $s_i$ and $c_i$ are empty could be implemented either as testing whether there are any strands in the subtube or more simply as whether there is any fluid in the subtube. The latter test might be more easily achieved in a video-controlled electrowetting system like PurpleDrop. Furthermore, although FIGS. 1 and 2 (and the Verilog code of Appendix 1) assume the mechanism for probing the ith bit is built into each tube (which might be sensible in a biochemical implementation), alternative embodiments are possible. Since this mechanism (of the kind in FIG. 9) may require magnetic and thermal hardware but is only used when a tube does SEPARATE operations (which is infrequent as illustrated in FIG. 3 and Table 1), those skilled in the art will realize it is possible to time multiplex the probing mechanism between several tubes.

Thus, the scope of the embodiments should be determined by the appended claims and their legal equivalents, rather than by the examples given.

Appendix 1: Verilog Simulation of a 5-bit DNA Memory Hierarchy

```
'define K 10 //number of total bits in strands, must be >=aw
'define aw 5 //number of address bits
'define NUMST (1<<'aw) //number of strands allows all possible addrs tested
    //modules define wires with size ['NUMST*('K+1)-1:0]
    //allow simulation of transport of 0 to 'NUMST strands together in a cycle
    //The ('K+1)bits of each strand indicates whether that strand exists
    //If('K+1)bit==0, that pos available in a combine to hold additional strand
    //Since NUMST large enough, if combine called properly always be room
    //In biochemical system, stand with particular address exists only in one place
    //In simulation, sometimes need temp copies of strands for a moment
    //Misusing combine with copies can cause COMBINE OVERFLOW (too many strands)
//following simulates demux and tube modules
// combine is a function (inside def of tube) which can be called with
// instanceoftube.combine(a,b)
// where a and b are wire['NUMST*('K+1)-1:0]
// can optimize instanceoftube.combine(a,b) to be a|b
// when it is known either a or b is empty
module demux (o1,o0,i,status);
    output o1,o0;
    input i;
    input status;
    wire ['NUMST*('K+1)-1:0] o0;
    wire ['NUMST*('K+1)-1:0] o1;
    wire ['NUMST*('K+1)-1:0] i;
    assign o0 =status ? 0 : i;
    assign o1 =status ? i : 0;
endmodule
module tube(o1,o0,i,cmd,status,clk);
    parameter BIT = 1;
    parameter LABEL = " ";
    parameter CUTOFF = (3<<BIT)>>1;
    output o1,o0;
    input i;
    input [2:0] cmd; //{force,s_i,f_i}
    output [1:0] status;
    input clk;
    reg ['NUMST*('K+1)-1:0] o1;
    reg ['NUMST*('K+1)-1:0] o0;
    wire ['NUMST*('K+1)-1:0] i;
    reg ['NUMST*('K+1)-1:0] t;
    assign status =
{getTubePop(t)>CUTOFF, (getTubePop(t)<=CUTOFF)&&(getTubePop(t) !=0));
    function ['K:0] getStrand;
        input['NUMST*('K+1)-1:0] in;
        input i;
        integer i;
```

Appendix 1: Verilog Simulation of a 5-bit DNA Memory Hierarchy

```
      begin
         getStrand = ((1<<('K+1))-1) & (in>>( ('K+1)*i));
      end
   endfunction
   function ['NUMST*('K+1)-1:0] putStrand;
      input ['NUMST*('K+1)-1:0] in;
      input i;
      input ['K:0] newstrand;
   integer i;
   begin
         putStrand = (( ~( ((1<<('K+1))-1)<<(('K+1)*i)) ) &in) |
(newstrand<<( ('K+1)*i));
      end
   endfunction
   function ['NUMST*('K+1)-1:0] initStrand;
      input 1;
      integer 1;
      reg ['NUMST*('K+1)-1:0] i1;
      integer i;
      begin
         if ((1>'K)||((1<<1)>'NUMST))
            begin
               $display("L too big");
               $stop;
            end
         i1 -\= 0;
         for (i=0; i< (1<<1); i=i+1)
            begin
               i1-putStrand(i1,i,i|(1<<'K));
            end
         initStrand =i1;
      end
   endfunction
   function ['NUMST*('K+1)-1:0] reverse;
      input['NUMST*('K+1)-1:0] in;
      reg ['NUMST*('K+1)-1:0] result;
      integer i,j;
      begin
         result = 0;
         j = 'NUMST-1;
         for (i=0; i< 'NUMST; i=i+1)
            begin
               result=putStrand(result,j,getStrand(in,i));
               j =j-1;
            end
         reverse = result;
      end
   endfunction
   function ['NUMST*('K+1)-1:0] compress;
      input['NUMST*('K+1)-1:0] in;
      reg ['NUMST*('K+1)-1:0] result;
      integer i,j;
      begin
         result = 0;
         j = 0;
         for (i=0; i< 'NUMST; i =i+1)
            begin
               if ((getStrand(in,i)>>'K)==1)
                  begin
                     result=putStrand(result,j,getStrand(in,i));
                     j = j+1;
                  end
            end
         compress = result;
      end
   endfunction
   function integer getTubePop;
      input['NUMST*('K+1)-1:0] in;
      integer i;
      integer count;
      begin
         count = 0;
         for (i=0; i< 'NUMST; i=i+1)
            begin
               if ((getStrand(in,i)>>'K)==1)
                  count = count + 1;
            end
```

Appendix 1: Verilog Simulation of a 5-bit DNA Memory Hierarchy

```
       getTubePop = count;
    end
 endfunction
 function ['NUMBT*('K+1)-1:0] combine;
    input['NUMST*('K+1)-1:0] i;
    input['NUMST*('K+1)-1:0] t;
    begin
       if (getTubePop(i)+getTubePop(t)>'NUMST)
          $display("COMBINE OVERFLOW");
       combine = compress(t)|reverse(compress(i));
    end
 endfunction
 function ['NUMST*('K+1)-1:0] H;
    input['NUMST*('K+1)-1:0] in;
    input kk;
    integer kk;
    reg ['NUMST*('K+1)-1:0] result;
    integer i;
    begin
       result = 0;
       for (i=0; i< 'NUMST; i =i+1)
          begin
             if (((getStrand(in,i)>>'K) ==1)&&((((getStrand(in,i)>>kk)&1) ==1)))
                begin
                   result=putStrand(result,i,getStrand(in,i));
                end
          end
       H = result;
    end
 endfunction
 function ['NUMST*('K+1)-1:0] L;
    input['NUMST*('K+1)-1:0] in;
    input kk;
    integer kk;
    reg ['NUMST*('K+1)-1:0] result;
    integer i;
    begin
       result = 0;
       for (i=0; i< 'NUMST; i=i+1)
          begin
             if (((getStrand(in,i)>>'K)==1)&&((((getStrand(in,i)>>kk)&1)==0)))
                begin
                   result=putStrand(result,i,getStrand(in,i));
                end
          end
       L = result;
    end
 endfunction
 function isEmpty;
    input['NUMST*('K+1)-1:0] in;
    integer i;
    reg isEmp;
    begin
       isEmp = 1;
       for (i=0; i< 'NUMST; i =i+1)
          begin
             isEmp = ((getStrand(in,i)>>'K)==0) & isEmp;
          end
       isEmpty =isEmp;
    end
 endfunction
 task displayStrands;
    input['NUMST*('K+1)-1:0] in;
    integer i;
    reg [K:0] mask;
    begin
       mask = (1<<'K)-1;
       for (i=0; i< 'NUMST; i =i+1)
          begin
             if ((getStrand(in,i) >>'K) ==1)
                $write("%d",getStrand(in,i)&mask);
          end
       $display(" ");
    end
 endtask
 task displayStrandsRaw;
    input['NUMST*('K+1)-1:0] in;
```

Appendix 1: Verilog Simulation of a 5-bit DNA Memory Hierarchy

```verilog
        integer i;
        begin
            for (i=0; i < 'NUMST; i =i+1)
                begin
                    //if ((getStrand(in,i)>>'K ==1)
                        $write("%b",getStrand(in,i));//&((1<<'K)-1)," ");
                end
            $display(" ");
        end
    endtask
    always @(posedge clk)
        begin
            case(cmd)
                3'b000: t <= combine(i,t);
                3'b001: t <= i;
                3'b010: t <= combine(i,U(t,BIT));
                3'b011: t <= combine(i,H(t,BIT));
                3'b100: t <= combine(i,t);
                3'b101: t <= i;
                3'b110: t <= i;
                3'b111: t <=i ;
            endcase
        end
    always @(t or cmd)
        begin
            case(cmd)
                3'b000: o0 = 0;
                3'b001: o0 = 0;
                3'b010: o0 = 0;
                3'b011: o0 = 0;
                3'b100: o0 = 0;
                3'b101: o0 = 0;
                3'b110: o0 = L(t,BIT);
                3'b111: o0 = t;//L(t,BIT);
            endcase
        end
    always @(t or cmd)
        begin
            case(cmd)
                3'b000: o1 = 0;
                3'b001: o1 = t;
                3'b010: o1 = L(t,BIT);
                3'b011: o1 = L(t,BIT);
                3'b100: o1 = 0;
                3'b101: o1 = t;
                3'b110: o1 = H(t,BIT);
                3'b111: o1 = 0;//H(t,BIT);
            endcase
        end
    always @(posedge clk)
        if (LABEL != " ")
            begin
                #1 $write($time," %s bit=%d stat=%b t=",LABEL,BIT,status);
                //displayStrandsRaw(t);
                displayStrands(t);
                $write($time, " %s cmd=%b i=",LABEL,cmd);
                displayStrands(i);
                $write($time," %s cmd=%b o1=",LABEL,cmd);
                //displayStrandsRaw(o1);
                displayStrands(o1);
                $write($time," %s o0=",LABEL);
                //displayStrandsRaw(o0);
                displayStrands(o0);
                $display(" ");
            end
    endmodule
    // comments in modules below give ref nums corresp. to figs
    module compare(ok4,rrcomb,o0,st,initialize,freeze,flush,clk); //2000
        output ok4; //200
        output rrcomb; //2309
        input o0; //1060
        input st; //5010-5012
        input initialize; //5002
        input freeze; //5003
        input flush; //5004
        input clk;
        reg ['NUMST*('K+1)-1:0] rrcomb; //2309
```

| Appendix 1: Verilog Simulation of a 5-bit DNA Memory Hierarchy |
|---|

```
        wire ['NUMST*('K+1)-1:0] o0; //1060
        wire ['NUMST*('K+1)-1:0] ok4; //200
        wire [2:0] st; //5010-5012
        wire initialize; //5002
        wire freeze; //5003
        wire flush; //5004
        wire clk;
        wire ['NUMST*('K+1)-1:0] rr3; //2303
        wire ['NUMST*('K+1)-1:0] rr2; //2203
        wire ['NUMST*('K+1)-1:0] rr1; //2103
        wire ['NUMST*('K+1)-1:0] ro4; //2430
        wire ['NUMST*('K+1)-1:0] ro3; //2330
        wire ['NUMST*('K+1)-1:0] cp0_1; //2030
        wire ['NUMST*('K+1)-1:0] cp0_0; //2020
        wire ['NUMST*('K+1)-1:0] dm0_0_0; //2060
        wire ['NUMST*('K+1)-1:0] dm0_0_1; //2070
        wire ['NUMST*('K+1)-1:0] dm0_1_0; //2080
        wire ['NUMST*('K+1)-1:0] dm0_1_1; //2090
        tube #(0," ") cmp0(cp0_1,cp0_0,o0,{~freeze,~freeze,1'b0},,clk);//2010=cmp0 tube
        demux dmx0_0(dm0_0_1, dm0_0_0, cp0_0, st[0]); //2040=dmx0_0
        demux dmx0_1(dm0_1_1, dm0_1_0, cp0_1, st[0]); //2050=dmx0_1
        wire ['NUMST*('K+1)-1:0] rj0 = dm0__0_1 | dm0_1_0;
           //2009 = combine(impl w|only 1 inp has strand)
        wire ['NUMST*('K+1)-1:0] ok0 = dm0_0_0 | dm0_1_1;
           //2008 = combine(impl w|only 1 inp has strand)
        wire ['NUMST*('K+1)-1:0] cp1_1; //2130
        wire ['NUMST*('K+1)-1:0] cp1_0; //2120
        wire ['NUMST*('K+1)-1:0] dm1_0_0; //2160
        wire ['NUMST*('K+1)-1:0] dm1_0_1; //2170
        wire ['NUMST*('K+1)-1:0] dm1_1_0; //2180
        wire ['NUMST*('K+1)-1:0] dm1_1_1; //2190
        wire ['NUMST*('K+1)-1:0] rj0oui-; //2102
        tube #(0," ") rej1(rj0out,rr1,rj0,{flush,flush,(~freeze)|flush},,clk); //2101
= rej1 tube
        tube #(1," ") cmp1(cp1_1,cp1_0,ok0,{~freeze,~freeze,1'b0},,clk); //2110
= cmp1 tube
           demux dmx1_0(dm1_0_1, dm1_0_0, cp1_0, st[1]); //2140
=dmx1_0 demux
           demux dmx1_1(dm1_1_1, dm1_1_0, cp1_1, st[1]); //2150
=dmx1_1 demux
        wire ['NUMST*('K+1)-1:0] rj1 =dm1_0_1 | dm1_1_0 | rj0out; //2109 =
combine(impl w|only 1 inp has strand)
        wire ['NUMST*('K+1)-1:0] ok1 =dm1_0_0 | dm1_1_1; //2108 =
combine(impl w|only 1 inp has strand)
        wire ['NUMST*('K+1)-1:0] cp2_1; //2230
        wire ['NUMST*('K+1)-1:0] cp2_0; //2220
        wire ['NUMST*('K+1)-1:0] dm2_0_0; //2260
        wire ['NUMST*('K+1)-1:0] dm2_0_1; //2270
        wire ['NUMST*('K+1)-1:0] dm2_1_0; //2280
        wire ['NUMST*('K+1)-1:0] dm2_1_1; //2290
        wire ['NUMST*('K+1)-1:0] rj1out; //2202
        tube #(0," ") rej2(rj1out,rr2,rj1,}flush,flush,(~freeze)|flush},,clk); //2201
= rej1 tube
        tube #(2," ") cmp2(cp2_1,cp2_0,ok1,}~freeze,~freeze,1'b0},,clk); //2210
= cmp2 tube
           demux dmx2_0(dm2_0_1, dm2_0_0, cp2_0, st[2[); //2240
= dmx2_0 demux
           demux dmx2_1(dm2_1_1, dm2_1_0, cp2_1, st[2]); //2250
=dmx2_1 demux
        wire ['NUMST*('K+1)-1:0] rj2 =dm2_0_1 | dm2_1_0 | rj1out; //2209 =
combine(impl w|only 1 inp has strand)
        wire ['NUMST*('K+1)-1:0] ok2 =dm2_0_0 | dm2_1_1; //2208 =
combine(impl w|only 1 imp has Strand)
        wire ['NUMST*('K+1)-1:0] rj3; //2302
        wire ['NUMST*('K+1)-1:0] ok3; //2320
        wire [1:0] okstat3; //2319
        tube #(0," ") rej3(rj3,rr3, rj2, {flush,flush,(~freeze)|flush],,clk);
           //2301, = rej3 tube
        tube #(0," ") cmp3(ok3,ro3, ok2, {flush,flush,(~freeze)|flush},okstat3,clk);
           //2310 = cmp3 tube
        reg flag; //2317
        // following always behavior implemented by logic 2318
        // with inputs okstat3 2319 and initialize 5002
        // producing output flag 2317
        always @(posedge clk)
           begin
              if (initialize == 1)
```

Appendix 1: Verilog Simulation of a 5-bit DNA Memory Hierarchy

```
              begin
                 flag <= 0;
              end
           else if (okstat3 != 0)
              begin
                 flag < =1;
              end
        end
     wire ['NUMST*('K+1)-1:0] rj3ok; //2307
     wire ['NUMST*('K+1)-1:0] rj3rj; //2306
     demux dmxrj(rj3ok, rj3rj, rj3, flag); //2305 = dmxrj demux
     wire ['NUMST*('K+1)-1:0] ok3ok =0k3 | rj3ok;
        //2308 = combine(impl w|only 1 imp has strand)
     tube #(0," ") cmp4(ok4,ro4, ok3ok,{flush,flush,(~freeze)|flush},,clk);
        //2410 = cmp4 tube
     //following combines require function calls in simulation
     //since multiple strands may be involved
     always @(rj3rj or rr3 or rr2 or rrl or ro4 or ro3)
        begin
           rrcomb = rj3rj;
           rrcomb = cmp4.combine(rr3,rrcomb);
           rrcomb = cmp4.combine(rr2,rrcomb);
           rrcomb = cmp4.combine(rr1,rrcomb);
           rrcomb = cmp4.combine(ro4,rrcomb);
           rrcomb = cmp4.combine(ro3,rrcomb);
        end
  endmodule
  module heirarchy(ok4,st,initialize,forcepipe,freeze,flush,ok4in,clk); //1000
     output ok4; //200
     input st; //5010-5012
     input initialize; //5002
     input forcepipe; //5001
     input freeze; //5003
     input flush; //5004
     input ok4in; //300
     input clk;
     wire ['NUMST*('K+1)-1:0] ok4;
     wire [2:0] st;
     wire initialize;
     wire forcepipe;
     wire freeze;
     wire flush;
     wire ['NUMST*('K+1)-1:0] ok4in;
     wire clk;
     initial //for simulation
        begin
           t4.t = 0;
           t3.t = 0;
           t2.t = 0;
           t1.t = 0;
           t0.t = 0;
           mem.t =t4.initStrand('aw);
        end
     wire ['NUMST*('K+1)-1:0] o5; //1560
     wire ['NUMST*('K+1)-1:0] o4; //1460
     wire ['NUMST*('K+1)-1:0] o3; //1360
     wire ['NUMST*('K+1)-1:0] o2; //1260
     wire ['NUMST*('K+1)-1:0] o1; //1160
     wire ['NUMST*('K+1)-1:0] o0; //1060
     wire ['NUMST*('K+1)-1:0] rt4; //1420
     wire ['NUMST*('K+1)-1:0] rt3; //1320
     wire ['NUMST*('K+1)-1:0] rt2; //1220
     wire ['NUMST*('K+1)-1:0] rt1; //1120
     wire ['NUMST*('K+1)-1:0] rt0; //1020
     reg ['NUMST*('K+1)-1:0] rcomb; //3020
     tube #0," ") mem(o5,,rcomb,(2'b00,initialize),,clk); //3000 = mem tube
     wire s4,s3,s2,s1,s0; //1440,1340,1240,1140,1040
     wire c4,c3,c2,c1,c0; //1450,1350,1250,1150,1050
     //following nine lines part of logic 4000
     wire z3 = (!s3)&&(!c3);
     wire z2 = (!s2)&&(!c2);
     wire z1 = (!s1)&&(!c1);
     wire z0 = (!s0)&&(!c0);
     wire f0 = 1;
     wire f1 = c0;
     wire f2 = s0&&z1;
     wire f3 = c0&&c1&&z2;
```

-continued

Appendix 1: Verilog Simulation of a 5-bit DNA Memory Hierarchy

```
wire f4 = s0&&cl&&z2&&z3;
tube #(4," ") t4(o4,rt4,o5,{(~freeze)&forcepipe|flush,(~freeze)&s4|flush,
        (~freeze)&f4|flush},{s4,c4},clk); //1410 = t4 tube
tube #(3," ") t3(o3,rt3,o4,{(~freeze)&forcepipe|flush,(~freeze)&s3|flush,
        (~freeze)&f3fflush},{s3,c3},clk); //1310 = t3 tube
tube #(2," ") t2(o2,rt2,o3,{(~freeze)&forcepipe|flush,(~freeze)&s2|flush,
        (~freeze)&f2|flush},{s2,c2},clk); //1210 = t2 tube
tube #(1," ") t1(o1,rt1,o2,{(~freeze)&forcepipe|flush,(~freeze)&s1|flush,
        (~freeze)&f1|flush},{sl,c1},clk); //1110 = t1 tube
tube #(0," ") t0(o0,rt0,o1,1,(~freeze)&forcepipe|flush,(~freeze)&s0|flush,
        (~freeze)&f0|flush},{s0,c0},clk); //1010 = t0 tube
wire ['NUMST*('K+1)-1:0] rrcomb; //3020
compare comp(ok4,rrcomb,o0,st,initialize,freeze,flush,clk);
        //2000 = earlier "compare" module
//following combines require function calls in simulation
//since multiple strands may be involved
always @(ok4in or rt4 or rt3 or rt2 or rt1 or rt0 or rrcomb)
    begin
        rcomb = t4.combine(rt4,ok4in);
        rcomb = t4.combine(rt3,rcomb);
        rcomb = t4.combine(rt2,rcomb);
        rcomb = t4.combine(rt1,rcomb);
        rcomb = t4.combine(rt0,rcomb);
        rcomb = t4.combine(rrcomb,rcomb);
    end
endmodule
// following simulates all possible starting (st) and ending (tries) addresses
// for each such case, verify the correct (and only those correct) strands
// appear in sequential order
module test;
    integer st;
    reg initialize;
    reg forcepipe;
    reg freeze;
    reg flush;
    reg clk;
    wire ['NUMST*('K+1)-1:0] ok4;
    heirarchy h(ok4, st[2:0],initialize,forcepipe,freeze,flush,ok4,clk) ;
    reg ['NUMST*('K+1)-1:0] ok4copy;
    integer ok4predict,ok4actual;
    integer numwrong;
    initial numwrong = 0;
    always @(posedge clk)
        begin
            ok4copy = h.t4.compress(ok4);
            if (h.t4.getTubePop(ok4copY) == 0)
                ok4predict =st;
            else
                begin
                    ok4actual =((1<<'K)-1) & h.t4.getStrand(ok4copy,0);
                    $write(ok4actual," ",ok4predict," ");
                    if (ok4actual !=ok4predict)
                        begin
                            $write("WRONG");
                            numwrong = numwrong + 1;
                        end
                    $display(" ");
                    ok4predict = ok4predict + 1;
                end
        end
    end
initial clk=0;
always #50 clk=~Clk;
integer i;
    integer starttime;
// uncomment to teat freezing pipeline
// always @(posedge clk)
// begin
// #1
// if (($time-starttime>2200)&($time-starttime<=2500))
// freeze = 1;
// else
// freeze = 0;
// end
    integer tries;
    initial
        begin
            flush = 0;
```

Appendix 1: Verilog Simulation of a 5-bit DNA Memory Hierarchy

```
            freeze = 0;
            initialize ft 0;
            forcepipe = 0;
            for (st = 0; st<'NUMST; st+=t+1)
               begin
                  for (tries=st; tries<'NUMST; tries = tries + 1)
                  begin
                     @(posedge clk) #0;
                     starttime = $time;
                     $display("st=",st," tries=",tries);
                     initialize = 1;
                     @(posedge clk) #0;
                     initialize = 0;
                     for (='aw-1; i>=3; i+=i-1)
                        begin
                           forcepipe =st[i];
                           @(posedge clk) #0;
                        end
                     forcepipe = 0;
                     wait(ok4actual===tries);
                     flush <= 1;
                     @(posedge clk) #0;
                     ok4actual ='bx;
                     @(posedge clk) #0;
                     @(posedge clk) #0;
                     @(posedge clk) #0;
                     flush <= 0;
                     @(posedge clk) #0;
                     @(posedge clk) #0;
                     //$stop;
                  end
               end
            $display("numwrong=",numwrong);
            $finish;
         end
endmodule
```

Appendix 2: Recursive C Simulation of a 5-bit DNA Memory Hierarchy

```
#include <stdio.h>
#include <stdlib.h>
#include <math.h>
//singrecur.c recursive functional def of DNA memory hierarchy with 5-bit addr
// little endian zero origin notation
// uses a bitset to represent tube contents.
// 0x00000001 is tube that contains strand with address 0
// 0x80000000 is tube that contains strand with address 0xlf
// 0xffffffff is tube that contains all strands (addresses 0 ... 0xlf)
int aw;
long double awscale;
//ratio is a real slightly less than 1.0 that when shifted over 2^aw bits
//acts as mask for portion of tube with bit k==0 to separate from
//portion where bit k==1 (works because bitset representation is ordered,
//even though a biochemical tube isn't)
long double ratio(int k)
{
   long double p;
   p = pow(2,pow(2,k));
   return p/(p+1);
}
//mask the low part that stays in the tube on a separate
long long L(long long t, int k)
{
   long long mask;
   mask = ((long long) floor((1--ratio(k))*awscale));
   return t & mask;
}
//mask the high part that leaves the tube on a separate
long long H(long long t, int k)
{
   long long mask;
   mask = ((long long) floor(ratio(k)*awscale));
   return t & mask;
}
```

Appendix 2: Recursive C Simulation of a 5-bit DNA Memory Hierarchy

```
//the mod function (which in actual imp might be computed by logic)
int f(int x, int k)
{ return ((x+k)%(1<<k))==0; }
//count how many strands in tube
int countbit(long long x)
{ int i,c=0;
  for (i=0; i<64; i ++)
  { if (x&(1LL<<i))
    c++;
  }
  return c;
}
//initialize tubes
long long initt(int x, int k, long long y)
    { if (k < -x)
        return 0;
      else if (x == 1-aw)
        return y;
      else if (x == 1-k)
        return L(initt(x-1,k+1,y),k+1);
      else if (x == 1-k)
        return H(initt(x-1,k,y),k);
      else
        return initt(x-1,k,y);
    }
//recursive definition of pipeline
//compared to actual implementation, very costly because
//naive non-tail recursion recomputes the same stuff over and over
long long t(int x, int k, long long y)
{ //printf("t %d %d\n",x,k);
  if (k>aw)
    return 0;
  else if (x <= 0)
    return initt(x,k,y);
  else if (countbit(t(x-1,k+1,Y)) > (1<<(k+1)) )
    return L(t(x-1,k+1,y),k+1);
  else if (f(x-1,k+1))
    return t(x-1,k+1,y);
  else if (!f(x-1,k))
    return t(x-1,k,y);
  else if (countbit(t(x-1,k,y)) > (1<<k) )
    return H(t(x-1,k,y),k);
  else
    return 0;
}
//for each cycle, print
// t_-1, result singleton set output in correct order
// t_0, set with up to two strands
// ...
// t_4, set with up to 32 strands
int main( )
{ long long yy;
  int x;
  aw = 5;
  awscale = pow(2,pow(2,aw));
  yy = ((long long) (awscale-1));
  for (x=1-aw; x<=(1<<aw); x++)
  { printf("%811x ",t(x,-1,yy));
    printf("%811x ",t(x,0,Yy));
    printf("%811x ",t(x,1,yy));
    printf("%811x ",t(x,2,yy));
    printf("%811x ",t(x,3,yy));
    printf("%811x\n",t(x,4,yy));
  }
  return 0;
}
/*
``` here is the correct output of this program:

| 0 | 0 | 0 | 0 | 0    | ffffffff |
|---|---|---|---|------|----------|
| 0 | 0 | 0 | 0 | ffff | ffff0000 |
| 0 | 0 | 0 | ff | ff00 | ffff0000 |
| 0 | 0 | f | f0 | ff00 | ffff0000 |
| 0 | 3 | c | f0 | ff00 | ffff0000 |
| 1 | 2 | c | f0 | ff00 | ffff0000 |
| 2 | c | 0 | f0 | ff00 | ffff0000 |

| Appendix 2: Recursive C Simulation of a 5-bit DNA Memory Hierarchy |
|---|

| | | | | | |
|---|---|---|---|---|---|
| 4 | 8 | f0 | 0 | ff00 | ffff0000 |
| 8 | 30 | c0 | 0 | ff00 | ffff0000 |
| 10 | 20 | c0 | 0 | ff00 | ffff0000 |
| 20 | c0 | 0 | ff00 | 0 | ffff0000 |
| 40 | 80 | 100 | 1000 | 0 | ffff0000 |
| 80 | 300 | c00 | f000 | 0 | ffff0000 |
| 100 | 200 | c00 | f000 | 0 | ffff0000 |
| 200 | c00 | 0 | f000 | 0 | ffff0000 |
| 400 | 800 | f000 | 0 | 0 | ffff0000 |
| 800 | 3000 | t000 | 0 | 0 | fff10000 |
| 1000 | 2000 | c000 | 0 | ffff0000 | 0 |
| 2000 | c000 | 0 | ff0000 | ff000000 | 0 |
| 4000 | 8000 | f0000 | f00000 | ff000000 | 0 |
| 8000 | 30000 | c0000 | f00000 | ff000000 | 0 |
| 10000 | 20000 | c0000 | f00000 | ff000000 | 0 |
| 20000 | c0000 | 0 | f00000 | ff000000 | 0 |
| 40000 | 80000 | f00000 | 0 | ff000000 | 0 |
| 80000 | 300000 | c00000 | 0 | ff000000 | 0 |
| 100000 | 200000 | c00000 | 0 | ff000000 | 0 |
| 200000 | c00000 | 0 | ff000000 | 0 | 0 |
| 400000 | 800000 | f000000 | f0000000 | 0 | 0 |
| 800000 | 3000000 | c000000 | f0000000 | 0 | 0 |
| 1000000 | 2000000 | c000000 | f0000000 | 0 | 0 |
| 2000000 | c000000 | 0 | f0000000 | 0 | 0 |
| 4000000 | 8000000 | f0000000 | 0 | 0 | 0 |
| 8000000 | 30000000 | c0000000 | 0 | 0 | ffffffff |
| 10000000 | 20000000 | c0000000 | 0 | ffff | ffff0000 |
| 20000000 | c0000000 | 0 | ff | ff00 | ffff0000 |
| 40000000 | 80000000 | f | f0 | ff00 | ffff0000 |
| 80000000 | 3 | c | f0 | ff00 | ffff0000 | after five (aw) cycles, the addresses start to appear in sequential order
0 (1), 1 (2), 2 (4), 3 (8), 4 (10), 5 (20), . . . 31 (80000000)
*/

Appendix 3: C Programs that Print "sc" Patterns for DNA Memory Hierarchy

```
/////////////////////////////////////////////////////
#include <stdio.h>
#include <stdlib.h>
#include <math.h>
// pipeinc1.c similar to DNA23 poster, except
//    only prints "s","o" instead of doing separate, combine
//    unlike DNA23,comment out "clk< . . ." part of if
//       this has effect of repeating after 2^n cycles instead of quitting
// clk starts at 0 has similar role as x starts at 1-n in later pipeinc*x.c
// n is same as aw in Verilog of appendix 1
// unlike most later pipeinc*x.c programs, this uses
//    little endian ONE origin tube numbers
//    this makes result appear in t_0 instead of t_-1
//    (note these comments use _ to indicate subscripts)
int main( )
{
   int clk,k,i,n,separatePos,combinePos;
   int iter;
   scanf("%d",&n);
   iter = (1<<n) +n;
   for (clk=0; clk<=iter-2; clk=clk+1)
   { for (k=1; k<=n; k=k+1)
      { for (i=0; i<=iter; i=i+1)
         {separatePos = n-k+i*(1<<k);
          combinePos = (1<<(k-1))+separatePos;
          if ((separatePos == clk)||(combinePos == clk))
             break;
         }
         if (separatePos==clk)//&&(clk<iter-(1<<(k-1))))
            printf("s"); //separate(t_k,t_k-1,t_k,t k=1);
         else if (combinePos==clk) //&i(clk<=iter-(1<(k-1))))
            printf("c"); //combine(t_k-1,t_k);
         else
            printf(" ");
      }
      printf("\n");
   }
}
```

Appendix 3: C Programs that Print "sc" Patterns for DNA Memory Hierarchy

```
/////////////////////////////////////////////////////
#include <stdio.h>
#include >stdlib.h>
#include <math.h>
// pipeinc2x.c same as pipeinc1.c except
// x starts at 1-n plays same as clk starts at 0
int main( )
{
   int x,k,i,n,SeparatePos,combinePos;
   int iter;
   scanf("%d",&n); .
   iter = (1<<n) +n;
   for (x=1-n; x<=iter-2+1-n; x=x+1)
   { for (k=1; k>=n; k=k+1)
      { for (i=0; i<=iter; i=i+1)
         {separatePos = n-k+i*(1<<k)+1-n;
          combinePos = (1<<(k-1))+separatePos;
          if ((separatePos == x)||(combinePos == x))
             break;
         }
         if (separatePos==x)
            printf("s"); //separate(t_k,t_k-1,t_k,t_k-1);
         else if (combinePos==x)
            printf("c"); //combine(t_k-1,t_k);
         else
            printf(" ");
      }
      printf("\n");
   }
}
/////////////////////////////////////////////////////
#include <stdio.h>
#include <stdlib.h>
#include <math.h>
// pipeinc3x.c same as pipeinc2x.c except
// little endian ZERO origin
// separatePos,combinePos replaced with mod calculation
```

Appendix 3: C Programs that Print "sc" Patterns for DNA Memory Hierarchy

```
int main( )
{
  int x,k,i,n;
  int iter;
  scanf("%d",&n);
  iter = (1<<n)+n;
  for (x=1-n; x<=iter-l-n; x=x+1)
  {//printf("%5d",x);
    for (k=0; k<=n-1; k=k+1)
    {
      if ((x+k)%(1<<(k+1))==0)
        printf("s"); //separate(t_k,t_k-1,t_k,t_k-1);
      else if ((x+k)%(1<<(k))==0)
        printf("c"); //combine(t_k-1,t_k);
      else
        printf(" ");
    }
    printf("\n");
  }
}
//////////////////////////////////////////////////////////////
#include <stdio.h>
#include <stdlib.h>
#include <math.h>
// pipeinc3xfun.c same as pipeinc3x except
// uses f_function to encapsulate mod calculation
int f(int x, int k)
  { return ((x+k)%(1<<(k)))==0; }
int main( )
{
  int x,k,i,n;
  int iter;
  scanf("%d"i&n);
  iter = (1<<n)+n;
  for (x=1-n; x<=iter-l-n; x=x+1)
  { //printf("%5d ",x);
    for (k=0; k<=-1; k=k+1)
    {
      if (f(x-1,k+1)) //((x+k)%(1<<(k+1))==0)
        printf("s"); //separate(t k,t_k-1,t_k,t_k-1);
      else if (f(x,k)) //((x+k)%(1<<(k))==0)
        printf("c"); //combine(t_k-1,t_k);
      else
        printf(" ");
    }
    printf("\n");
  }
}
//////////////////////////////////////////////////////////////
#include <stdio.h>
#include <stdlib.h>
#include <math.h>
// pipeinc4xfun.c same as pipeinc3xfun.c except
// logic expressed in terms of f_k and s_k
int f_function(int x, int k)
  { return ((x+k)%(1<<(k)))==0; }
int main( )
{
    int x,k,i,n,separatePos,combinePos;
    int iter;
    int f[100],s[100];
    scanf("%d",&n);
    iter = (1<<n)+n;
    for (x=1-n; x<=iter-l-n; x=x+1)
    { //printf("%5d ",x);
      for (k=0; k<=n-1; k=k+1)
      {
        f[k] = f_function(x,k);
        s[k] =f function(x-1,k+1);
        if (s[k]) //(f(x-1,k+1))
          printf("s"); //separate(t_k,t_k-1,t_k,t_k-1);
        else if (f[k]&&(!s[k])) //(f(X,k))
          printf("c"); //combine(t_k-1,t_k);
        else
          printf(" ");
      }
      printf("\n");
    }
}
#include <stdio.h>
#include <stdlib.h>
#include <math.h>
// pipeinc5xfun.c same as pipeinc4xfun.c except
// s_k (full occupancy of t_k) computed from f_k+1 in prey cyc
// needs initial fn; since not reset final pipe stages differ
// decision tests f_k then USeS s_k to decide "s" or "c"
int f_function(int x, int k)
  { return ((x+k)%(1<<(k)))==0; }
int main( )
{
    int x,k,n;
    int iter;
    int f[100],s[100];
    scanf("%d",&n);
    iter = (1<<n)+n;
    for (k==0; k<=n-1; kk+1)
      f[k] = 0==1;
    f[n] = 1==1;
    for (x=1-n; x<=iter-l-n; x=x+1)
    { //printf("%5d ",x);
      for (k=0; k<=n-1; k=+1)
      { s[k] = f[k+1];
        f[k] = f_function(x,k);
        if (f[k])
        { if (s[k])
            printf("s"); //separate(t_k,t_k-1,t_k,t_k);
          else
            printf("c"); //combine(t_k-1,t_k);
        }
        else
          printf(" ");
      }
      printf("\n");
      f[n] = 0;
    }
}
//////////////////////////////////////////////////////////////
#include <stdio.h>
#include <stdlib.h>
#include <math.h>
// pipeinc6xfunsc.c same as pipeinc5xfun.c except
// s_i and c_i calculated as in FIG. 6, but without force
int f_function(int x, int k)
  { return ((x+k)%(1<<(k)))==0; )
int main( )
{
    int x,k,n;
    int iter;
    int f[100],s[100],c[100];
    scanf("%d",&n);
    iter = (1<<n)+n;
    for (k=0; k<=n-1; k=k+1)
    { f[k] = 0==1;
      s[k] = 0==1;
      c[k] = 0==1;
    }
    f[n] = 1==1;
    s[n] = 1==1;
    for (x=1-n; x<=iter-l-n; x=x+1)
    { //printf("%5d ",k);
      for (k=0; k<=n-1; k=k+1)
      {c[k] = s[k] || ((!f[k])&&c[k]);
        s[k] = f [k+1];
        f[k] = f_function(x,k);
        if (f[k])
        { if (s[k])
            printf("s"); //separate(t_k,t_k-1,t_k,t_k);
          else
            printf("c"); //combine(t_k-1,t_k);
        }
        else
          printf(" ");
      }
```

Appendix 3: C Programs that Print "sc" Patterns for DNA Memory Hierarchy

```
        for (k=0; k<=n-1; k=k+1)
            printf("%d%d ",s[k],c[k]);
        printf("\n");
        f[n] =0;
    }
}
////////////////////////////////////////////////////////////
#include <stdio.h>
#include <stdlib.b>
#include <math.h>
// pipeinc6xlogeqn.c same as pipeinc6xfunsc.c except
// output intended to print logic equations like those in Table 3
// input n=4 prints logic equations up to f15
// input n=5 prints logic equations up to f31
// input n=6 prints logic equations up to f63, etc.
//
int f_function(int x, int k)
    {return ((x+k)%(1<<(k)))==0; }
int main( )
{
    int i,x,k,n;
    int iter;
    int f[100],s[100],c[100];
    scanf("%d",&n);
    iter = (1<<n)+n;
    for (k=0; k<=n-1; k=k+1)
    { f[k] = 0==1
        s[k] = 0==1;
        c[k] = 0==1;
    }
    f[n] = 1==1;
    s[n] = 1==1;
    for (x=1-n; x<=iter-1-n; x=x+1)
    {i = iter-n - x;
        if (x>0) printf("f%d=",i);
        for (k=0; k<=n-1; k=k+1)
        { c[k] =s(k) || ((!f[k])&&c(k+);
            s[k] = f[k+1];
            f[k] = f_function(x,k);
            if (s[k])
                { if ((k<i)&&(x>0))
                    printf("s%d",k);
                }
            else if (c[k])
                { if ((k<i)&&(x>0))
                    printf("c%d",k);
                }
            else
                { if ((k<i)&&(x>0))
                    printf("z%d",k);
                }
        }
        for (k=n; k<=iter-n; k=k+1)
        { if ((k<i)&&(x>0))
            printf("z%d",k);
        }
        if (x>0) printf("\n");
        f[n] = 0;
    }
}
////////////////////////////////////////////////////////////
#include <stdio.h>
#include <stdlib.h>
#include <math.h>
// pipeinc7xfunsc.c same as pipeinc6xfun.c except
// s[ ] and c[ ] computed via recurrence/state machine method
// f[ ] computed via logic equations (up to n=5)
// if statements similar to pipeinc4xfun.c
int f_function(int x, int k)
    {return ((x+k)%(1<<(k)))==0; )
int main( )
{
    int x,k,n;
    int iter;
    int f[100],s[100],c[100],z[100];
    scanf("%d",&n);
    iter = (1<<n)+n;
    for (k=0; k<=n-1; k=k+1)
    { f[k] = 0==1
        s[k] = 0==1
        c[k] = 0==1;
    }
    f[n] = 1==1;
    for (x=1-n; x<=iter-1-n; x=x+1)
    { printf("%5d ",x);
        for (k=0; k<=n-1; k=k+1)
        {c[k] = s[k] || ((!f[k])&&c[k]);
            s[k] = s[k+1]||f[k+1];
            z [1] = (!s[1]) && (!c[1]);
            z [2] = (!s[2]) && (!c[2]);
            z [3] = (!s[3]) && (!c[3]);
            if (k==0) f[0] = 1== 1;
            if (k==1) f[1] = c[0];
            if (k==2) f[2] = s[0]&&z[1];
            if (k==3) f[3] - c[0]&&c[1]&&z[2];
            if (k==4) f[4] = s[0]&&C[1]&&z[2]&&z[3];
            if (s[k])
                printf("s"); //separate(t_k,t_k-1,t_k,t_k);
            if ((!s[k])&&f[k])
                printf("c"); //combine(t_k-1,t_k);
            if ((!s[k])&&(!f[k]))
                printf(" ");
        }
        for (k=0; k<=n-1; k=k+1)
            printf(" %d%d",s[k],c[k]);
        for (k=0; k<=n-1; k=k+1)
            printf(" %d",f[k]);
        printf("\n");
        f[n] =0;
    }
}
////////////////////////////////////////////////////////////
#include <stdio.h>
#include <stdlib.h>
#include <math.h>
// pipeinc8xfunsc.c same as pipeinc7xfun.c except
// allows initialization of high order three bits
// by force technique (as in FIGS. 4-5) for s_i and c_i
int f_funttion(int x, int k)
    { return ((x+k)%(1<<(k)))==0; }
int main( )
{
    int x,k,n;
    int iter;
    int f[100],s[100],c[100],z[100];
    int xinit,force,force4,force3,force2;
    scanf("%d",&n);
    scanf("%d",&xinit);
    force4 = 1&(xinit>>4);
    force3 = 1&(xinit>>3);
    force2 = 1&(xinit>>2);
    printf("highorder=%d%d%d\n",force4,force3,force2);
    iter = (1<<n)+n;
    for (k=0; k<=n-1; k=k+1)
    { f[k] = 0==1;
        s[k] = 0==1;
        c[k] = 0==1;
    }
    f[n] = 1==1;
    for (x=xinit+1-n; x<=iter-1-n; x=x+1)
    { printf("%5d ",x);
        if (x==xinit-3) force = force4;
        else if (x==xinit-2) force = force3;
        else if (x==xinit-1) force = force2;
        else force = 0;
        for (k=0; k<=n-1; k=k+1)
        { c(k) = (s[k] && (force==0)) || ((!f[k])&&c[k]);
            s[k] = s[k+1]||f[k+1];
            z[1] = (!s[1])&&(!c[1]);
            z[2] = (!s[2])&&(!c[2]);
            z[3] = (!5[3])&&(!c(3));
            if (k==0) f[0] = 1==1
            if (k==1) f[1] = c[0];
            if (k==2) f[2] = s[0]&&z[1];
```

Appendix 3: C Programs that Print "sc" Patterns for DNA Memory Hierarchy

```
        if (k==3) f[3] = s[0]&&c[1]%&&z[2]
        if (k==4) f[4] = s[0]&&c[1]&&z[2]&&z[3];
        if (s[k])
            printf("8"); //teparate(t_k,t_k-1,t_k,t_k);
        if ((!s[k])&&f[k])
            printf ("c"); //combine(t_k-1,t_k);
        if ((!s[k]) && (!f[k]))
            printf (" ") ;
    }
```

Appendix 3: C Programs that Print "sc" Patterns for DNA Memory Hierarchy

```
    for (k=0; k<=n-1; k=k+1)
        printf(" %d%d", s[k] , c[k]);
    for (k=0; k<=n-1; k=k+1) '
        printf(" %d", f [k] ) ;
    printf(" force=%d\n", force);
    f[n] = 0;
    }
}
```

Appendix 3: Exhaustive Java Simulation of Pipeline Initialization for 11-bit Address

```
import java.lang.Integer;
public class StkPlayllc(
//note: capital S3 and S5 to avoid naming conflict with Stickx
static boolean s0,s1,52,S3,s4,S5,s6,s7,s8,s9,s10;
static boolean c0,c1,c2,c3,c4,c5,c6,c7,c8,c9,c10;
static boolean z1,z2,z3,z4,z5,z6,z7,z8,z9;
static boolean f1,f2,f3,f4,f5,f6,f7,f8,f9,f10;
static int aw, Mt, Mts, M, temp, PCIR;
//****sticker modified to have tubePop (except staple) 5/27/18
//it current_read_pos = 0;
//boolean read_safely = true;
static boolean produce_listing = true;
static int 1 = 2; //form.user_1.value;
static int k = 4; //form.user_k.value;
static int numTubes = 4;//form.user_numTubes.value;
static String user_fmt = "2d1b1b";
//static String alpha = "abcdefghijklmnopqrstuvwxyz";
static int numStrands = 0;
static int maxStrands = 3600000;
//static String[ ] s3 = new String[maxStrands];
//static String[ ] s5 = new String[maxStrands];
static into strand = new int[maxStrands];
static int[ ] tubeNum = new int[maxStrands];
static int[ ] tubePop = new int[maxStrands]; // 5/27/18 faster for Ghosal-Sakar
public static void mywriteln(String s)
{
    System.out.println(s);
}
public static void myerr (String s)
{
    mywriteln(s);
}
public static void mywrite(String s) {
    System.out.print(s);
}
// simulated Pascal strings
public static String mycopy(String s, int posit, int len)
( //System.out.println("posit =" +posit+" len ="+len+" s ="+s);
    if (posit < 1 || len < 0)
        return(" ");
    else if (posit+len > s.length())
        return(s.substring(posit-1));
    else
        return(s.substring(posit-1,posit+len-1));
}
public static int mypos(String s1, String s2)
{
    //if (s2 == " " && s1 != " ")
    //if (s2.equals(" ") && (!s1.equals(" "))
    if (s2.1ength( ) == 0 && s1.length( ) != 0)
        return (0);
    else
        return(s2.indexOf(s1) + 1);
}
public static String deblank(String s)
{
    int i,posnb;
    posnb = -1;
    for (i=s.length( )-1; i >=0; i--)
    {
        if (!(s.substring(i,i +1).equals(" ")))
            posnb = i;
    }
```

Appendix 3: Exhaustive Java Simulation of Pipeline Initialization for 11-bit Address

```java
    if (posnb ! = -1)
        return(s.substring(posnb,s.length( )));
    else
        return(s);
}
public static String shortenline(String line)
{
    int posblank;
    posblank =mypos(" ", line);
    if (posblank ==0) posblank = line.length( ) + 1;
    return(mycopy(line, posblank+1, line.length( )));
}
/*
    function to remove right blanks from line
*/
public static String trim(String line) /*string to be trimed*/
{
    int i, /*pos in string*/
        nonbl ;/*pos of rightmost non-blank*/
    nonbl = line.length( ); /*in case no blanks in string, don't trim*/
    for (i = 1; i <= line.length({); i ++ )
        {
            if (!(mycopy(line, i, 1).equals(" "))) nonbl = i;
        }
    return(mycopy(line, 1, nonbl));
} /*trim*/
public static int getK( )
    { return k-0; }
public static int getL( )
    { return 1-0; }
public static int getNumTubes( )
    { return numTubes-0; }
public static int getNumStrands( )
    {int ii,count=0;
    for (i i=0; ii < numStrands; ii++)
    { if (tubeNum[ii] ! = -1)
        count++;
    }
    return (count);
}
public static int getTubePop(int i)
    { int ii;
        int count=0;
        if (i >=numTubes)
            mywriteln("tube " +i+" too big");
        return tubePop[i];
}
public static String toBinary(int x, int k)
    { int i;
        String s =" ";
        int mask =1<<k;
        for (i = k-1; i>=0; i--)
        { if ((x&(1<<i))! =0)
            s = s + "1";
        else
            s = s + "0";
        mask = mask >> 1;
    }
    return s;
}
public static String toReverseBinary(int x, int k)
    { int i;
        String s=" ";
        int mask = 1<<k;
        for (i =k-1; i >=0; i--)
        { if ((x&(1<<i))! =0)
            s = "1" + s;
        else
            s = "0" + s;
        mask = mask >> 1;
    }
    return s;
}
public static String getfirstfmt(String fmt) {
        int posd = mypos("d", fmt);
        if (posd==0)
            posd = fmt.length( );
```

Appendix 3: Exhaustive Java Simulation of Pipeline Initialization for 11-bit Address

```java
        int posb = mypos("b", fmt);
        if (posb==0)
            posb = fmt.length( );
        int posr = mypos("r", fmt);
        if (posr==0)
        posr = fmt.length( );
        int posfmt = Math.min(Math.min(posd, posb), posr);
        return(mycopy(fmt, 1, posfmt));
    }
public static String formatConvert(int x, int k, String fmt)
{
    if ((k <=0)||(fmt.length( )==0))
        return " ";
    String firstfmt =getfirstfmt(fmt);
    Integer firstk =new Integer(mycopy(firstfmt, 1, firstfmt.length( )−1));
    String firstx = " " +(x>>(k−firstk));
    if (mycopy(firstfmt,firstfmt.length( ),1).equals("b"))
        firstx = toBinary(new Integer(firstx),firStk);
    else if (mycopy(firstfmt,firstfmt.length (),1).equals("r"))
        firstx = toReverseBinary(new Integer(firstx),firstk);
    String restConvert = " "+formatConvert(x&((1<<(k−firstk))−1), k−firstk,
mycopy(fmt, firstfmt.length( ) +1, fmt.length( )));
    if (restConvert.length( ) == 0)
        return " "+firstx;
    else
        return " "+firstx +"_" +restConvert;
}
public static String getTube(int i)
    { String s=" ";
      int ii;
      String convertedStrand;
      if (i>=numTubes)
          mywriteln("tube " +i +" too big");
      else
      for (ii = 0; ii < numStrands; ii++)
      {if (tubeNum[ii]==i)
          {convertedStrand = formatConvert(strand[ii],k,user_fmt);
              if (s.length( )==0)
                  s =" " + convertedStrand;
              else
                  s =s + "," +convertedStrand;
          }
      }
      return s;
    }
public static String tubeToString( )
    {int i;
      String s =" ";
      for (i=0; i <numTubes i ++)
          s = s + " " + i + ":{" + getTube(i) + "} ";
      return s;
    }
public static void listOn( )
    { produce_listing = true; //form.list_button.value ="List Off";
    }
public static void listOff( )
    { produce_listing = false; //form.1ist_button.value ="List On";
    }
public static void displayAfter( )
    {
        if (produce_listing)
            mywriteln(tubeToString( ));
    }
public static void display( )
    {
mywriteln(" "+tubeToString( ));
    }
public static void init(int i)
    { int ii;
      if ( i>numTubes)
          mywriteln("i too big");
      else if ((1<<1) > maxStrands-numStrands)
          myerr("exceed maxStrands");
      else
          {
              for (ii=numStrands; ii < numStrands +(1<<l); ii ++)
                  { tubeNum[ii] = i;
```

Appendix 3: Exhaustive Java Simulation of Pipeline Initialization for 11-bit Address

```
                strand[ii] = ii-numStrands;
            }
            numStrands += 1<<1;
            tubePop[i] += 1<<1; //5/27/18
        }
        if (produce_listing)
            mywrite("init");
        displayAfter( );
    }
public static void initCustom(int i; int v)
    { if (i >numTubes) mywriteln("i too big");
        else if (v>=(1<<k)) mywriteln("v too big");
        else
            {
                tubeNum[numStrands] = i;
                strand[numStrands] = v;
                numStrands += 1;
                tubePop[i] += 1; // 5/27/18
                if (numStrands >= maxStrands)
                    myerr("exceed maxStrands");
            }
        if (produce_listing)
            mywrite("cust");
        displayAfter( );
    }
public static void set(int i, int kk)
    { int ii;
        if (kk>=k)
            mywriteln("k too big");
        int temp = 1<<kk;
        if (i>=numTubes)
            mywriteln("tube " +i+" too big");
        else
            for (ii=0; ii < numStrands; ii++)
            { if (tubeNum[ii] == i)
                strand[ii] |= temp;
            }
        if (produce_listing)
            mywrite("set ");
        displayAfter( );
    }
public static void clear(int i; int kk)
    { int ii;
        if (kk>=k)
            mywriteln("k too big");
        int temp = ~(1<<kk) ;
        if (i>=numTubes)
            mywriteln("tube "+i+" too big");
        else
            for (ii=0; ii < numStrands; ii++)
            { if (tubeNum[ii] == i)
                strand[ii] &= temp;
            }
        if (produce_listing)
            mywrite("clr ");
        displayAfter( );
    }
public static void separate(int i, int j, int k)
    { separate3(i, j, j, k); }
public static void separate3(int i1, int i0, int j, int kk)
    { int ii;
        if (kk>=k)
            mywriteln("k too big");
        int temp = 1<<kk;
        if ((i1>=numTubes) || (i0>numTubes) || (j>numTubes))
            mywriteln("tube "+i1+" or "+i0+" or "+j+" too big");
        else
            for (ii=0; ii < numStrands; ii++)
            {if (tubeNum[ii] == j)
                if ((strand[ii]+&temp) == temp)
                    {tubeNum[ii] = i1; tubePop[j]--; tubePop[i1]++; } // 5/27/18
                else
                    {tubeNum[ii] = i0; tubePop+j+--; tubePop[i0]++; } // 5/27/18
            }
        if (produce_listing)
            mywrite("sep ");
        displayAfter( );
```

Appendix 3: Exhaustive Java Simulation of Pipeline Initialization for 11-bit Address

```java
    }
public static void discard(int i)
    { int ii;
        if (i>=numTubes)
            mywriteln("tube "+i+" too big");
        else
        for (ii=0; ii < numStrands; ii++)
        { if (tubeNum[ii] == i)
                tubeNum[ii] = -1;
        }
        tubePop[i] = 0; // 5/27/18
        if (produce_listing)
            mywrite("dis ");
        displayAfter( );
    }
public static int removeOneStrand(int i)
    {
        int ii,v=-1;
        if (i>=numTubes)
            mywriteln("tube "+i+" too big");
        else
        {
        for (ii = 0; ii < numStrands; ii++)
        { if (tubeNum[ii]==i)
                {
                    v = strand[ii];
                    tubeNum[ii] = -1;
                    tubePop[i]--; // 5/27/8
                    break;
                }
            }
        }
        return v;
    }
public static void combine(int i, int j)
    { int ii;
        if ((i>=numTubes) || (j>numTubes))
            mywriteln("tube "+i+" or "+j+" too big");
        else
        for (ii=0; ii < numStrands; ii++)
        { if (tubeNum[ii] == j)
                tubeNum[ii] = i;
        }
        tubePop[i] += tubePop[j]; // 5/27/18
        tubePop[j] = 0;
        if (produce_listing)
            mywrite("comb");
        displayAfter( );
    }
public static void split(int i, int j)
    { int ii;
        if ((i>=numTubes) || (j>numTubes))
            mywriteln("tube "+i+" or "+j+" too big");
        else
        for (ii=0; ii < numStrands; ii++)
        {if ((tubeNum[ii] == j)&&(Math.random( )>0.5))
                {tubeNum[ii] = i; tubePop[j]--; tubePop[i]++;} //5/27/18
        }
        if (produce_listing)
            myWrite("split");
        displayAfter( );
    }
public static void splitDeterministic(int i, int j)
    { int ii;
        boolean odd=false;
        if ((i>=numTubes) || (j>numTubes))
            mywriteln("tube "+i+" or "+j+" too big");
        else
        for (ii=0; ii < numStrands; ii++)
        { if (tubeNum[ii] == j) .
            { if (odd) (tubeNum[ii] = i; tubePop[j]--; tubePop[i]++;) //5/27/18
                odd = !odd;}
        }
        if (produce_listing)
            mywrite("splitDet");
        displayAfter( );
}
```

Appendix 3: Exhaustive Java Simulation of Pipeline Initialization for 11-bit Address

```
//****end of stickers with tubePop 5/27/18
public static void xortest( )
{ int i;
  System.out.println("Java Extended Stickers: xor");
  produce_listing = true;
  l = 3;
  k = 5;
  numTubes = 4;
  user_fmt = "2d3d";
  discard(0);
  init(0); //tube0=k-bit strands;1 bits init'ed;k-1 bits=0\n";
  separate(1,0,0); //if bit0==0 stay tube0;else tube1\n";
  separate(3,1,1); //if bit1==0 stay tubel;else tube3\n";
  separate(2,0,1); //if bit1==0 stay tube0;else tube2\n";
  combine(1,2); //pour tube 2 into 1\n";
  for (i-getL( );i<=getL( )+1;i++)//javascript loop example\n";
     set(1,i); //sets bits 1,1+1 (ie2,3)\n";
  combine(0,3); //pour tube 3 into 0\n";
  combine(0,1); //pour tube 1 into 0\n";
  mywriteln("result: "+getTube(0));
  mywriteln("number: "+getTubePop(0));
}
public static int getnN(int x)
{ int i,nN;
  nN=0;
  for (i=1; i<=aw-2; i++) //don't do MSB
  { if ((x&(1<<i)) != 0)
     { if ((i+(((1<<i)--1)&x)) >= (1<<i) }
        nN = i;
     }
  }
  return nN;
}
public static void gennN(int start)
{ int nN,iI;
  nN = getnN(start);
  //mywriteln(form,"start nN="+nN);
  for (iI = 1; iI<=(nN+1-(1<<nN)+((1<<nN)-1&start)); iI++)
  (//mywrite(form,start+" iI="+ii+" ");
  if (iI == 1)
     combine(Mts+nN,nN+1);
     //mywriteln(form,"combine("+(0+Mts+nN)+","+(l+nN)+")");
  else
     separate3(2+nN-iI,Mts+nN-iI+1,Mts+nN-iI+2,2+nN-iI);
     //mywriteln(form,"separate3("+(2+nN-iI)+","+
     //(0+Mts+nN-iI+1)+","+(0+Mts+nN-iI+2)+","+(2+nN-iI)+")");
  }
}
public static void printnN(int start)
{ int nN,iI;
  nN = getnN(start.);
  mywriteln("start nN="+nN);
  for (i{ = 1; ii<=(nN+1-(1<<nN)+((1<<nN)-1&start)); iI++)
  (mywrite(start+" iI="+iI+" ");
  if (ii == 1)
     //Combine(Hts+nN,nN+1);
     mywriteln("combine("+(0+Mts+nN)+","+(1+nN)+")");
  else
     //separate3(2+nN-iI,Mts+nN-iI+1,Mts+nN-iI+2,2+nN-iI);
     mywriteln("separate3("+(2+nN-iI)+","+
     (0+Mts+nN-iI+1)+0,0+(0+Mts+nN-iI+2)+","+(2+nN-iI)+")0);
  }
}
public static void fetchpipe(int addr)
{int i;
  combine(Mts+aw-1,M);
  for (i=aw-1; i>1; i=i-1)
  fseparate(temp,addr,i/*+aw*/);
     if (getTubePop(temp)>0)
        separate3(Mts+i-1,M,Mts+i,i); .
     else
        separate3(Mt+i,Mts+i-1,Mts+i,i);
     combine(addr,temp);
  }
  separate(temp,addr,1/*+aw*/); //maybe redund to extra iteration above
  if (getTubePop(temp)>0)
     separate3(Mts,M,Mts+1,1);
```

Appendix 3: Exhaustive Java Simulation of Pipeline Initialization for 11-bit Address

```
    else
        separate3(Mt+1,Mts,Mts+1,1);
    combine(addr,temp);
    separate(temp,addr,0/*+aw*/);
    if (getTubePop(temp)>0)
        separate3(Mt+0,M,Mts+0,0);
    combine(addr,temp);
}
public static void flipTubeState(boolean f, boolean s, int i)
{if (i==0)
    {
        if (s0)
            {//mywrite(form,"S0");
                separate3(Mt+0,temppipe /*2*Mts*/,Mts+0,0);}
        else
            {//mywrite(form,"C0");
                combine(temppipe /*2*Mts*/,Mt+0);}
    }
    else
    {if (f)
     {if (s)
        {//mywrite(form,"S"+i+" ");
            separate3(Mt+i, Mts+i−1, Mts+i, i);}
     else
        {//mywrite(form,"C"+i+" ");
            combine(Mts+i−1,Mt+i);}
     }
    }
}
public static void iter ()
{
    s0 = getTubePop(Mts+0)>0;
    s1 = getTubePop(Mts+1)>0;
    s2 = getTubePop(Mts+2)>0;
    s3 = getTubePop(Mts+3)>0;
    s4 = getTubePop(Mts+4)>0;
    s5 = getTubePop(Mts+5)>0;
    s6 = getTubePop(Mts+6)>0;
    s7 = getTubePop(Mts+7)>0;
    s8 = getTubePop(Mts+8)>0;
    s9 = getTubePop(Mts+9)>0;
    s10 = getTubePop(Mts+10)>0;
    c0 = getTubePop(Mt+0)>0;
    c1 = getTubePop(Mt+1)>0;
    c2 = getTubePop(Mt+2)>0;
    c3 = getTubePop(Mt+3)>0;
    c4 = getTubePop(Mt+4)>0;
    c5 = getTubePop(Mt+5)>0;
    c6 = getTubePop(Mt+6)>0;
    c7 = getTubePop(Mt+7)>0;
    c8 = getTubePop(Mt+8)>0;
    c9 = getTubePOp(Mt+9)>0;
    c10 = getTubePop(Mt+10)>0;
    //mywriteln(form,"C0="+c0+"; C1="+c1+"; C2="c2+"; C3="+c3+"; C4="*c4+";");
    //mywriteln(form,"S0="+s0+"; S1="+s1+"; S2="+s2+"; S3="+s3+"; S4="+s4+";");
    //mywriteln(form,"f1="+f1+"; f2="+f2+"; f3="+f3+";f4="+f4+";)");
    z1 = (!s1)&&(!c1);
    z2 = (!s2)&&(!c2);
    z3 = (!s3)&&(!c3);
    z4 = (!s4)&&(!c4);
    z5 = (!s5)&&(!c5);
    z6 = (!s6)&&(!c6);
    z7 = (!s7)&&(!c7);
    z8 = (!s8)&&(!c8);
    z9 = (!s9)&&(!c9);
    f1 = c0;
    f2 = s0&&z1;
    f3 = c0&&c1&&22;
    f4 = s0&&c1&&z2&&z3;
    f5 = c0&&sl&&z2&&z3&&z4;
    f6 = s0&&z1&&c2&&z3&&z4&&z5;
    f7 = c0&&cl&&c2&&z3&&z4&&z5&&z6;
    f8 = s0&&cl&&c2&&23&&24&&z5&&t6&&z7;
    f9 = c0&&sl&&c2&&z3&&z4&&z5&&z6&&z7&&z8;
    f10 = s0&&z1&&s2&&z3&&z4&&z5&&z6&&z7&&z8&&z9;
    flipTubeState(true,s0,0);
    flipTubeState(f1,s1,1);
```

Appendix 3: Exhaustive Java Simulation of Pipeline Initialization for 11-bit Address

```
        flipTubeState(f24s2,2);
        flipTubeState(f3,S3,3);
        flipTubeState(f4,s4,4);
        flipTubeState(f5,S5,5);
        flipTubeState(f6,s6,6);
        flipTubeState(f7,s7,7);
        flipTubeState(f8,58,8);
        flipTubeState(f9,s9,9);
        flipTubeState(f10,s10,10);
    }
    static iht temppipe, cmp0, cmp1, addr0, addr1;
    public static void comparePCIR( )
    {int i;
        for (1=0; i<=3; i=i+1)
        ( combine(addr0,addr1);
            separate(addr1,addr0,i);
            if ( (((getTubePop(addr1)>0)!=(getTubePop(cmp1+i)>0)) &&
                  ((getTubePop(addr1)>0)||(getTubePop(addr0)>0)) )
            { combine(M,cmp0+i);
                combine(M,cmp1+i);
            }
            else
            { separate3(cmp1+i+1,cmp0+i+1,cmp0+i,i+1);
                separate3(cmp1+i+1,cmp0+i+1,cmp1+i,i+1);
            }
        }
        if ((getTubePop(cmp0+4)>0)||(getTubePop(cmp1+4)>0))
            { combine(PCIR,addr0);
                combine(PCIR,addr1);
            }
        combine(2*Mts,cmp0+4);
        combine(2*Mts,cmp1+4);
        separate3(cmp1+0,cmp0+0,temppipe,0);
    }
    public static void fetchpipeplay2(int addr)
    {int i;
        combine(Mts+aw-1,M);
        for (i=aw-1; 1>0; i=1-1)
        {separate(temp,addr,i/*+aw*/);
            if ((getTubePop(temp)>0)&&(i+>=4))
                separate3(Mts+i-1,M,Mts+i,i);
            else
                separate3(Mt+i,Mts+i-1,Mts+i,i);
            combine(addr,temp);
        }
    }
    public static void fetchpipeplay(int addr)
    {int i;
        boolean 1b1=false, 1b2=false, 1b3=false, 1b4=false,allow=true;
        combine(Mts+aw-1,M);
        for (i=aw-1; 1>0; 1=1-1)
        {separate(tempiaddr,i/*+aw*/);
            if ((getTubePop(temp)>0)&&allow)
                {separate3(Mts+i-1,M,Mts+i,1);
                    if (i>=8) 1b4 |= true;
                    else if (i>=4) 1b3 |= true;
                    else if (i>=2) 1b2 |= true;
                    else if (i>=1) lbl 1= true;
                    if ((i==4)&&1b4) allow=false;
                    if ((i==3)&&1b3) allow=false;
                    if ((i==2)&&1b2) allow=false;
                    if ((i==1)&&1b1) allow=false; }
                else
                    { separate3(Mt+i,Mts+i-1,Mts+i,i);
                        1b4 = false;
                    1b3 = false;
                    1b2 = false;
                    1b1 = false; }
            combine(addritemp);
        }
        if (allow)
        { separate(temp,addr,0/*+aw*/);
        if (getTubePop(temp)>0)
        separate3(Mt+0,M,Mts+0,0);
        combine(addr,temp);
        }
        System.out.println(allow+" "+1b4+" "+1b3+" "+1b2+" "+1b1);
```

Appendix 3: Exhaustive Java Simulation of Pipeline Initialization for 11-bit Address

```
}
public static void nletest( )
{int i,jj,iii,start;
    System.out.println("Java Extended Stickers: NLE");
    produce_listing = false;
    user_fmt = "lld";
    aw = 11;
    l = aw;
    k = aw;
    numTubes = 2*aw+18;
    Mt = 0;
    Mts =aw;
    M = 2*aw+2;
    temp = 2*aw+1;
    PCIR = 2*aw+3;
    temppipe = 2*aw+4;
    addr0 = 2*aw+5;
    addr1 = 2*aw+6;
    cmp0 = 2*aw+7;
    cmp1 = 2*aw+12;
    init(Mts*2-1);
    double.avgdone=0.0,donetime=0,0;
    for (start=0;start<(1<<aw); start++)
    {
       for(i=0;i<=M;i++)
          if (i != 2*Mts-1) combine(2*Mts-1, i);
    discard(PCIR);
    initCustom(PCIR,start);
    System.out.print(start+" ");
    fetchpipeplay(PCIR); // ***** replace With fetchpipeplay2 for alternative
    combine(addr0,PCIR);
    donetime = 0.0;
    for(jj=start;jj<(1<<aw)+16;jj++)
    { iter( );
       comparePCIR( );
       if (((getTubePop(2*Mts)+start)==(1<<aw)) && (donetime==0.0))
          {System.out.println(start+" DONETIME="+(0+jj-(1<<aw)));
            donetime =jj-(1<<aw);
            avgdone += donetime;
            //System.out.println("AVGDONE="+(avgdone/(Math.pow(2.0,aw))));
          }
    }
    for(iii=0;iii<2*aw;iii++)
    { if (getTubePop(iii)>0)
        mywrite("WRONG ");
    }
    if ((getTubePop(2*Mts)+start) != (1<<aw))
       mywriteln("BADCOUNT "+getTubePop(2*Mts)+" "+(0+getTubePop(2*Mts)+start));
    display( );
    }
    System.out.println("AVGDONE="+(avgdone/(Math.pow(2.0,aw))));
}
public static void main(String [ ] arg)
    {
       nletest( );
    }
}
```

I claim:

1. A method for accessing oligonucleotide strands from a memory hierarchy, consisting of a memory tube and a plurality of pipeline tubes, wherein each of said strands encodes information including aw address bits, whereby each of said address bits is able to be probed via biochemical hybridization, the index i is an integer whose value varies between one less than said aw and zero, and ith of said pipeline tubes is referred to as $t_i$ tube, and wherein said memory hierarchy outputs into a $t_{-1}$ tube a sequence of subsets of said strands in sequential order determined by said address bits, said method including the steps of:
  initializing including transferring said strands from said memory tube to a $t_{aw-1}$ tube;
  repeating for each pipeline cycle, the steps of:
    performing for each said value of said index i, the steps of:
      obtaining status signals, including $s_i$ status;
      generating an $f_i$ command;
      separating a portion of said strands from $t_i$ tube based on the ith of said address bits into a $t_{i-1}$ tube while leaving remaining strands in said $t_i$ tube when said $s_i$ status is asserted; and
      transferring said remaining strands from said $t_i$ tube into said $t_{i-1}$ tube when said $s_i$ status is unasserted and said $f_i$ command is asserted; and
    processing said strands in said $t_{-1}$ tube.

2. The method of claim 1 whereby each said $t_i$ tube in said plurality of said pipeline tubes is composed of an $s_i$ subtube and a $c_i$ subtube, and wherein said step of transferring further includes transferring said remaining strands from said $c_i$ subtube to a $s_{i-1}$ subtube when said $f_i$ command is asserted and said $s_i$ status is unasserted, and wherein said step of separating further includes separating said portion of said strands from said $s_i$ subtube based on the ith of said address bits into said $s_{i-1}$ subtube while transferring said remaining strands from said $s_i$ subtube into said $c_i$ subtube when said $s_i$ status is asserted, and wherein said step of obtaining said status signals further includes the steps of:
  asserting said $s_i$ status if said $s_i$ subtube is not empty; and
  asserting a $c_i$ status if said $c_i$ subtube is not empty.

3. The method of claim 2 wherein said step of generating said $f_i$ command includes the steps of:
  asserting $z_i$ status when said $s_i$ status is unasserted and said $c_i$ status is unasserted; and
  evaluating a logic equation from Table 3 that corresponds to said value of said index i as a function of said $s_i$ status, said $c_i$ status, and said $z_i$ status, yielding said $f_i$ command.

4. The method of claim 1 wherein said step of obtaining said status signals further includes the steps of:
  measuring the approximate number of strands in said $t_i$ tube;
  asserting said $s_i$ status if said approximate number is large relative to a predetermined midpoint capacity of said $t_i$ tube; and
  asserting a $c_i$ status if said approximate number is nonzero and less than or equal to said midpoint capacity of said $t_i$ tube.

5. The method of claim 4 wherein said step of generating said $f_i$ command includes the steps of:
  asserting $z_i$ status when said $S_i$ status is unasserted and said $c_i$ status is unasserted; and
  evaluating a logic equation from Table 3 that corresponds to said value of said index i as a function of said $s_i$ status, said $c_i$ status, and said $z_i$ status, yielding said $f_i$ command.

6. The method of claim 1 wherein said step of processing further includes the step of returning said strands from said $t_{-1}$ tube to said memory tube, and wherein said step of initializing further includes the steps of:
  obtaining a high-order target;
  flushing said tubes to return all said strands to said memory tube;
  transferring said strands from said memory tube to said $t_{aw-1}$ tube; and
  repeating for each bit of said high-order target, the steps of:
    separating said portion of said strands from said $t_i$ tube based on said ith of said address bits into a $t_{i-1}$ tube while leaving said remaining strands in said $t_i$ tube when zero equals the value of said bit of said high-order target; and
    separating said portion of said strands from said t tube based on said ith of said address bits into said memory tube while transferring said remaining strands into said $t_{i-1}$ tube when one equals said value of said bit of said high-order target.

7. The method of claim 6 wherein said step of initializing is performed by an electronic computer that requests access to said sequence of subsets of said strands starting at said high order target, and wherein said step of processing further includes repeating for a number of iterations of said pipeline cycle determined by said electronic computer the steps of:
  electrochemically sampling a portion of said strands in said $t_{-1}$ tube, thereby recovering from said strands in said $t_{-1}$ tube said information as electronic information, including electronic address bits corresponding to said address bits;
  storing at least some of said electronic information into an electronic memory; and
  manipulating said electronic information from said electronic memory by said electronic computer.

8. The method of claim 7 wherein said step of initialization further includes the step of assigning said high order target to an x count, wherein said step of obtaining said status signals includes the step of copying a $f_{i+1}$ command from previous said pipeline cycle, yielding said $s_i$ status, and wherein said step of generating said $f_i$ command includes the steps of:
  calculating two raised to said value of said index i, yielding a power of two;
  calculating the sum of said value of said index i plus the value of said x count modulo said value of said power of two, yielding a modulo count;
  asserting said $f_i$ command if the value of said modulo count equals zero; and
  incrementing said x count.

9. A method for accessing oligonucleotide strands from a memory hierarchy, consisting of a memory tube and a plurality of pipeline tubes, wherein each of said strands encodes information including aw address bits, whereby each of said address bits is able to be probed via biochemical hybridization, the index i is an integer whose value varies between one less than said aw and zero, and the ith of said pipeline tubes is referred to as $t_i$ tube, and wherein said memory hierarchy outputs into a tube a sequence of subsets of said strands in sequential order determined by said address bits starting at a high order target, said method including the steps of:
  initializing including the steps of:
    obtaining said high-order target;
    flushing said tubes to return all said strands to said memory tube;

transferring said strands from said memory tube to said $t_{aw-1}$ tube; and unasserting a force command on conclusion of said step of initializing; and repeating for each pipeline cycle, the steps of:

performing for each value of said index i, the steps of:

obtaining status signals, including an $s_i$ status;

generating an $f_i$ command;

first separating a portion of said strands from said $t_i$ tube based on the ith of said address bits into a $t_{i-1}$ tube while leaving remaining strands in said $t_i$ tube when said $s_i$ status is asserted and said force command is unasserted;

second separating said portion of said strands from said $t_i$ tube based on said ith of said address bits into said memory tube while transferring said remaining strands into said $t_{i-1}$ tube when said $s_i$ status is asserted and said force command is asserted; and transferring said remaining strands from said $t_i$ tube into said $t_{i-1}$ tube when said $s_i$ status is unasserted and said $f_i$ command is asserted; and processing said strands in said tube, said step of initializing further including the step of repeating for each bit of said high-order target, concurrently to repetition of said pipeline cycle, the steps of:

unasserting said force command when zero equals the value of said bit of said high-order target; and asserting said force command when one equals said value of said bit of said high-order target.

10. The method of claim 9 wherein said step of initializing is performed by an electronic computer that requests access to said sequence of subsets of said strands starting at said high order target, and wherein said step of processing further includes repeating for a number of iterations of said pipeline cycle determined by said electronic computer the steps of:

electrochemically sampling a portion of said strands in said $t_{-1}$ tube, thereby recovering from said strands in said $t_{-1}$ tube said information as electronic information, including electronic address bits corresponding to said address bits;

storing at least some of said electronic information into an electronic memory; and manipulating said electronic information from said electronic memory by said electronic computer.

11. The method of claim 10 wherein said step of initializing further includes giving said $s_i$ status, and a $c_i$ status initial values, wherein said step of generating said $f_i$ command includes evaluating a logic equations from Table 3 that corresponds to said value of said index i as a function of said $s_i$ status, said $c_i$ status, and a $z_i$ status, yielding said $f_i$ command, and wherein said step of obtaining said status signals includes the steps of:

keeping said $c_i$ status asserted when said $c_i$ status was asserted in the previous pipeline cycle and said $f_i$ command was unasserted in said previous pipeline cycle;

asserting said $c_i$ status when said $s_i$ status was asserted in said previous pipeline cycle and said force command was unasserted in said previous pipeline cycle;

asserting said $s_i$ status when $f_{i+1}$ command from said previous pipeline cycle was asserted;

asserting said $s_i$ status when $s_{i+1}$ status from said previous pipeline cycle was asserted; and asserting said $z_i$ status when said $s_i$ status is unasserted and said $c_i$ status is unasserted.

12. The method of claim 9 wherein said step of initializing further includes the steps of resetting a state variable, and of obtaining a low-order target consisting of ceil($\log_2$(aw)) bits, and wherein said step of processing further includes the steps of:

comparing said low-order target against the low-order portion of said address bits of said strands in said $t_{-1}$ tube;

setting said state variable when said low-order target matches said low-order portion;

returning said strands from said $t_{-1}$ tube to said memory tube until said state variable is set; and processing only those of said strands in said $t_{-1}$ tube which are not returned to said memory tube.

13. The method of claim 12 wherein said step of processing further includes decoding the non-address bits of said strands in said $t_{-1}$ tube as a machine language instruction; and executing said machine language instruction by carrying out biochemical reactions in one or more user tubes.

14. The method of claim 13 wherein said step of decoding further includes distinguishing between a branch instruction and a non-branch instruction, and wherein said step of executing said machine language instruction further includes triggering said initialization step using portions of said branch instruction as said high-order target and said low-order target.

15. The method of claim 14 whereby each said $t_i$ tube in said plurality of said pipeline tubes is composed of an $s_i$ subtube and a $c_i$ subtube, and wherein said step of transferring further includes transferring said remaining strands from said $c_i$ subtube to a $s_{i-1}$ subtube when said $f_i$ command is asserted and said $s_i$ status is unasserted, and wherein said step of separating further includes separating said portion of said strands from said $s_i$ subtube based on the ith of said address bits into said $s_{i-1}$ subtube while transferring said remaining strands from said $s_i$ subtube into said $c_i$ subtube when said $s_i$ status is asserted, and wherein said step of obtaining said status signals further includes the steps of:

asserting said $s_i$ status if said $s_i$ subtube is not empty; and asserting a $c_i$ status if said $c_i$ subtube is not empty.

16. The method of claim 15 wherein said step of generating said $f_i$ command includes the steps of:

asserting $z_i$ status when said $s_i$ status is unasserted and said $c_i$ status is unasserted; and evaluating a logic equation from Table 3 that corresponds to said value of said index i as a function of said $s_i$ status, said $c_i$ status, and said $z_i$ status, yielding said $f_i$ command.

17. The method of claim 16, whereby said user tubes include $a_0$ tube and $a_1$ tube, wherein said step of decoding further includes distinguishing COMBINE0, COMBINE1, SEPARATE1 and SET1 instructions, and wherein said step of executing said machine language instruction further includes:

combining strands from said $a_0$ tube into a tube specified by said machine language instruction and combining strands from said $a_1$ tube into said $a_0$ tube when said machine language instruction is said COMBINE1;

combining strands from said tube specified by said machine language instruction into said $a_0$ tube when said machine language instruction is said COMBINE0;

separating said strands from said $a_0$ tube based on a bit position specified by said machine language instruction into said $a_1$ tube when said machine language instruction is said SEPARATE1 while leaving remaining strands in said $a_0$ tube; and setting a bit position specified by said machine language instruction in said strands from said $a_0$ tube via biochemical hybridization when said machine language instruction is said SET1.

18. A memory hierarchy accessing oligonucleotide strands, wherein each of said strands encodes information including aw address bits, whereby the value of each of said address bits is able to be probed via biochemical hybridization, wherein the number of said strands is nr, the integer parameter r is greater or equal to one, and the integer parameter n is no more than two raised to the power of said aw, including:
   a memory tube capable of holding all said strands;
   a pipeline of aw tubes, wherein the first of said aw tubes, known as $T_1$, can hold at least nr of said strands, is connected to said memory tube and is operative for probing the first of said aw address bits, wherein the second of said aw tubes, known as $T_2$, can hold at least nr/2 of said strands, is connected to said $T_1$ and is operative for probing the second of said aw address bits, and wherein the third of said aw tubes, known as $T_3$, can hold at least nr/4 of said strands, is connected to said $T_2$ and is operative for probing the third of said aw address bits, wherein said pipeline continues similarly to the last of said aw tubes, known as $T_{aw}$, wherein said $T_{aw}$ can hold at least 2r of said strands, is connected to $T_{aw-1}$, and is operative for probing the last of said aw address bits;
   a processing unit for holding at least r of said strands, wherein said processing unit is connected to said $T_{aw}$; and
   logic for receiving external control inputs and for receiving a plurality of status from said aw tubes, and in response for generating a plurality of commands to said aw tubes, whereby said commands cause said tubes to probe said strands and to selectively transfer subsets of said strands through said pipeline, thereby providing said processing unit with a sequence of said subsets of said strands having sequential patterns of said address bits as guided by said external control inputs.

19. The memory hierarchy of claim 18 wherein one of said aw tubes, known as $T_i$, operative for probing the ith of said aw address bits further comprises:
   an input pipe capable of transferring n' of said strands, wherein the integer parameter n' is said integer parameter r times two raised to the power aw−i+1;
   an output pipe capable of transferring n'/2 of said strands;
   a chamber capable of holding n' of said strands;
   a $S_i$ status output to said logic, wherein said $S_i$ status is asserted when said chamber contains more than approximately 3n'/4 of said strands; and
   a $C_i$ status output to said logic, wherein said $C_i$ status is asserted when said chamber is not empty but contains less than approximately 3n'/4 of said strands,
wherein said chamber operative for separating a portion of said n' strands via said output pipe based on said ith of said address bits while leaving remaining strands in said chamber when said $S_i$ status is asserted, operative for transferring said remaining strands from said chamber via said output pipe and for transferring said n' strands via said input pipe to said chamber when said $S_i$ status is unasserted and said logic asserts an $F_i$ command, operative for combining said n' strands transferred via said input pipe with said remaining strands in said chamber when said $S_i$ command is unasserted and said $F_i$ status is unasserted.

20. The memory hierarchy of claim 19 wherein said logic generates said $F_i$ command according to the logic equations in Table 3, whereby said $F_i$ is synonymous with $f_{aw-i}$, said $S_i$ is synonymous with $s_{aw-i}$, and said $C_i$ is synonymous with $c_{aw-i}$.

21. The memory hierarchy of claim 18 wherein one of said aw tubes, known as $T_i$, operative for probing the ith of said aw address bits further comprises:
   an input pipe capable of transferring n' of said strands, wherein the integer parameter n' is said integer parameter r times two raised to the power aw−i+1
   an output pipe capable of transferring n'/2 of said strands
   a first chamber capable of holding n' strands,
   an $S_i$ status output to said logic, wherein said $S_i$ status is asserted when said first chamber is not empty
   a second chamber capable of holding n'/2 of said strands,
   a $C_i$ status output to said logic, wherein said $C_i$ status is asserted when said second chamber is not empty,
wherein said first chamber is operative for separating a portion of said n' strands via said output pipe based on said ith of said address bits while transferring remaining strands to said second chamber when said $S_i$ status is asserted, and for transferring said n' strands via said input pipe to said first chamber when said $S_i$ status is unasserted, and wherein said second chamber is operative for receiving said remaining strands from said first chamber when said $S_i$ status is asserted, and for transferring said remaining strands from said second chamber via said output pipe when said $S_i$ status is unasserted and said $F_i$ command is asserted.

22. The memory hierarchy of claim 21 wherein said logic generates said $F_i$ command according to the logic equations in Table 3, whereby said $F_i$ is synonymous with $f_{aw-i}$, said $S_i$ is synonymous with $s_{aw-i}$, and said $C_i$ is synonymous with $c_{aw-i}$.

23. The memory hierarchy of claim 18 wherein one of said aw tubes, known as $T_i$, operative for probing the ith of said aw address bits further comprises:
   an input pipe capable of transferring n' of said strands, wherein the integer parameter n' is said integer parameter r times two raised to the power aw−i+1;
   an output pipe capable of transferring n'/2 of said strands;
   a return pipe capable of returning said strands to said memory tube;
   an external flush command for indicating when all said strands should return to said memory tube via said return pipe;
   an external force command for indicating the initial high-order address bits to be received by said processing unit;
   a chamber capable of holding n' of said strands;
   a $S_i$ status output to said logic, wherein said $S_i$ status is asserted when said chamber contains more than approximately 3n'/4 of said strands; and
   a $C_i$ status output to said logic, wherein said $C_i$ status is asserted when said chamber is not empty but contains less than approximately 3n'/4 of said strands,
wherein said chamber is operative for returning said strands from said chamber to said memory tube via said return tube when said flush command is asserted, operative for separating a portion of said n' strands via said output pipe based on said ith of said address bits while leaving remaining strands in said chamber when said $S_i$ status is asserted, said force command is unasserted and said flush command is unasserted, operative for separating a portion of said n' strands to said memory tube via said return pipe based on said ith of said address bits while transferring remaining strands via said output pipe when said $S_i$ status is asserted, said force command is asserted and said flush command is unasserted, operative for transferring said strands from said chamber via said output pipe and for transferring said n' strands via said input pipe to said chamber when said $S_i$ status is unasserted and said flush command is unasserted and said logic asserts an $F_i$ command, operative for combining said n' strands transferred via said input pipe with said strands in said chamber when said $S_i$ status is unasserted and said $F_i$ command is unasserted and said flush command is unasserted.

24. The memory hierarchy of claim 23 wherein said logic generates said $F_i$ command according to the logic equations in Table 3, whereby said $F_i$ is synonymous with $f_{aw-i}$, said $S_i$ is synonymous with $s_{aw-i}$, and said $C_i$ is synonymous with $c_{aw-i}$.

25. The memory hierarchy of claim 24 wherein said processing unit is further operative for returning said subsets of said strands to said memory tube via said return pipe.

26. The memory hierarchy of claim 25 further including comparison unit connected between said $T_{aw}$ and said processing unit, operative for returning said subsets of said strands to said memory tube via said return pipe from the time an external initialization command is asserted until the time said subset of said strands have low-order address bits that match external bits, and operative for passing through said subsets of said strands from said $T_{aw}$ to said processing unit at all other times.

* * * * *